US011052072B2

(12) United States Patent
Chen et al.

(10) Patent No.: US 11,052,072 B2
(45) Date of Patent: *Jul. 6, 2021

(54) PYRAZOLO[4,3-C] QUINOLINE DERIVATIVES FOR INHIBITION OF β-GLUCURONIDASE

(71) Applicant: Kaohsiung Medical University, Kaohsiung (TW)

(72) Inventors: Yeh-Long Chen, Kaohsiung (TW); Tian-Lu Cheng, Kaohsiung (TW); Cherng-Chyi Tzeng, Kaohsiung (TW); Chih-Hua Tseng, Kaohsiung (TW); Ta-Chun Cheng, Kaohsiung (TW); Kai-Wen Cheng, Kaohsiung (TW); Wei-Fen Luo, Kaohsiung (TW)

(73) Assignee: KAOHSIUNG MEDICAL UNIVERSITY, Kaohsiung (TW)

(*) Notice: Subject to any disclaimer, the term of this patent is extended or adjusted under 35 U.S.C. 154(b) by 0 days.

This patent is subject to a terminal disclaimer.

(21) Appl. No.: 16/711,623

(22) Filed: Dec. 12, 2019

(65) Prior Publication Data

US 2020/0113878 A1    Apr. 16, 2020

Related U.S. Application Data

(62) Division of application No. 15/577,201, filed as application No. PCT/US2016/034379 on May 26, 2016.

(60) Provisional application No. 62/166,322, filed on May 26, 2015.

(51) Int. Cl.
| | |
|---|---|
| *A61K 31/437* | (2006.01) |
| *A61K 45/06* | (2006.01) |
| *C07D 471/04* | (2006.01) |
| *A61P 35/00* | (2006.01) |
| *A61K 31/055* | (2006.01) |
| *A61K 31/03* | (2006.01) |

(52) U.S. Cl.
CPC .......... *A61K 31/437* (2013.01); *A61K 31/055* (2013.01); *A61K 45/06* (2013.01); *A61P 35/00* (2018.01); *C07D 471/04* (2013.01); *A61K 31/03* (2013.01)

(58) Field of Classification Search
CPC ...... C07D 471/04; A61K 31/437; A61P 35/00
USPC ........................................................ 514/303
See application file for complete search history.

(56) References Cited

U.S. PATENT DOCUMENTS 5,192,768 A    3/1993  Suzuki et al.
2012/0329785 A1*  12/2012  Thormann ........... C07D 471/04
                                                    514/221

FOREIGN PATENT DOCUMENTS

WO    WO 2005/028474 A2    3/2005

OTHER PUBLICATIONS

Cedric Leroy et al , Quantitative phosphoproteomics reveals a cluster of kinases that mediate SRC invasive activity in advanced colon carcinoma cells. (Year: 2010).*
Minoru Ono et al, Phosphorylation of Beta-Glucuronidases from human normal liver and heptoma by a cAMP-dependent protein kinase. (Year: 1968).*
Ta-Chun Cheng et al. Discovery of Specific Inhibitors for intestinal *E. coli* Beta-Glucuronidase through In Silico virtual screening . . . (Year: 2014).*
Ramadan Ahmed Mekheimer Fused Quinoline Heterocyclces. (Year: 2006).*
Bret D. Wallace, et al. Alleviating Cancer Drug Toxicity by Inhibiting a Bacterial Enzyme, www.sciencemag.org, vol. 330, Nov. 5, 2010, American Association for the Advancement of Science, 1200 New York Avenue NW, Washington, DC 20005, Science 330, pp. 831-835, (2010) DOI: 10.1126/science.1191175, 6 pgs.
Cheng et al., "Discovery of Specific Inhibitors for Intestinal *E. coli* beta-Glucuronidase through In Silico Virtual Screening," The Scientific World Journal. Aug. 27, 2014, p. 1-8, vol. 2015, Article ID 740815, Hindawi Publishing Corporation, http://dx.doi.org/10.1155/2015/740815.
European Patent Office, Extended European Search Report, E.P. Application No. 16800725.0-1116/3302060, Kaohsiung Medical University, dated Oct. 31, 2018, 8 pgs.
International Search Report and Written Opinion for International Application No. PCT/US2016/034379 dated Aug. 23, 2016. (10 pages).
National Center for Biotechnology Information. PubChem Compound Database; CID=11087003, https://pubchem.ncbi.nlm.nih.gov/compound/11087003 (accessed Feb. 5, 2018).
National Center for Biotechnology Information. PubChem Compound Database; CID=11140796, https://pubchem.ncbi.nlm.nih.gov/compound/11140796 (accessed Aug. 23, 2016).
Ramadan Ahmed Mekheimer, (2001) Fused Quinoline Heterocycles. II. First Synthesis of 1,2,3,4,5,6-Hexaazaaceanthrylenes and 5,7,8,10a,11-Pentaazabenzo[a]-Fluorenes, Synthetic Communications: An International Journal for Rapid Communication of Synthetic Organic Chemistry, vol. 31, No. 13, pp. 1971-1982, DOI: 10.1081/SCC-100104413, Taylor & Francis Informa Ltd Registered in England and Wales Registered No. 1072954 Registered office: Mortimer House, 37-41 Mortimer Street, London W1T 3JH, UK, Published Online Nov. 9, 2006. 14 pgs.

(Continued)

*Primary Examiner* — Rita J Desai
(74) *Attorney, Agent, or Firm* — Hannah Tien

(57) ABSTRACT

The present invention provides novel pyrazolo[4,3-c]quinoline derivatives exhibiting specifically inhibition activity to microbiota β-glucuronidase, whereby providing potent activities to prevent chemotherapy-induced diarrhea (CID) of cancers. Therefore, the compounds of the present invention can be used as (1) chemotherapy-adjuvant to prevent chemotherapy-induced diarrhea (CID) and enhance chemotherapeutic efficiency of cancers; (2) health-food supplement to prevent the carcinogens induced colon carcinoma.

4 Claims, 7 Drawing Sheets
(2 of 7 Drawing Sheet(s) Filed in Color)

(56) References Cited

OTHER PUBLICATIONS

Kai-Wen Cheng, et al., Specific Inhibition of Bacterial β-Glucuronidase by Pyrazolo[4,3-c]quinoline Derivatives via a pH-Dependent Manner to Suppress Chemotherapy-Induced Intestinal Toxicity, Nov. 9, 2017, pp. 9222-9238, vol. 60, DOI: 10.1021/acsjmedchem. 7b00963, Journal of Medicinal Chemistry, American Chemical Society, ACS Publications.

* cited by examiner

PYRAZOLO[4,3-C] QUINOLINE DERIVATIVES FOR INHIBITION OF β-GLUCURONIDASE

CROSS-REFERENCE TO RELATED APPLICATIONS

The application is a divisional of U.S. patent application Ser. No. 15/577,201, filed on Nov. 27, 2017, which is a 371 of International Application No. PCT/US2016/034379, filed on May 26, 2016, which claims the benefit of U.S. Provisional Patent Application No. 62/166,322, filed on May 26, 2015, the disclosures of which are incorporated herein in their entirety by reference.

FIELD OF THE INVENTION

The present invention relates to a new compound for inhibition of β-glucuronidase. Particularly, the present invention provides a pyrazolo[4,3-c]quinoline derivative specifically inhibit microbiota β-glucuronidase.

BACKGROUND OF THE INVENTION

Camptothecin, an alkaloid isolated from *Camptotheca acuminata* [Wall, M. E.; Wani, M. C.; Cook, C. E.; Palmer, K. H.; McPhail, A. T.; Sim, G. A. *J. Am. Chem. Soc.* 1966, 88, 3888-3890; Werbovetz, K. A.; Bhattacharjee, A. K.; Brendle, J. J.; Scovill, J. P. *Bioorg. Med. Chem.* 2000, 8, 1741-1747] has been found to possess significant anticancer activities [Wall, M. E. *Camptothecin and taxol: discovery to clinic. Med. Res. Rev.* 18, 299-314 (1998)]. However, camptothecin also exhibited marked toxicity and poor bioavailability [J. F. Pizzolato, L. B. Saltz, *Lancet* 361, 2235 (2003)] which limited its clinical use. Topotecan and irinotecan (CPT-11) are semisynthetic products derived from camptothecin and are currently in clinical use for the treatment of overian cancer and non-small cell lung cancers (topotecan) and colon cancer (CPT-11) [Mathijssen, R. H., Loos, W. J., Verweij, J. & Sparreboom, A. *Pharmacology of topoisomerase I inhibitors irinotecan (CPT-11) and topotecan. Curr. Cancer Drug Targets* 2, 103-123 (2002)]. CPT-11 is a prodrug, with a carbamate-linked dipiperidino group which is removed in vivo to produce the active metabolite SN-38. It is then glucuronidated in the liver by uridine diphosphate (UDP)-ghicuronosyltransferases to form inactive SN38-glucuronide (SN-38G) which is then excreted via the biliary ducts into the gastrointestinal (GI) tract. Once in the intestines, SN-38G serves as a substrate for microbiota β-glucuronidase (eβG) and was hydrolyzed to bioactive SN-38 which plays an essential role in diarrhea [Takasuna, K. et al. *Optimal antidiarrhea treatment for antitumor agent irinotecan (CPT-1 Ij-induced delayed diarrhea. Cancer Chemother. Pharmacol.* 58, 494-503 (2006); Yong, W. P., et al. *Effects of ketoconazole on glucuronidation by UDP-glucuronosyltransferase enzymes. Clin. Cancer Res.* 11, 6699-6704 (2005)].

Certain eβG inhibitors have been discovered to reduce bioactivation of SN-38G and alleviate CPT-11 induced diarrhea [Benson, A. B., 3rd et al. *Recommended guidelines for the treatment of cancer treatment-induced diarrhea. J. Clin. Oncol.* 22, 2918-2926 (2004)]. The CPT-11 is metabolized in the liver to SN-38G which is then excreted into the gastrointestinal (GI) tract and hydrolyzed by eβG to bioactive SN-38, leading to the intestinal damage and diarrhea and the structures of CPT-11, SN-38 and SN-38G are disclosed in Takasuna, K. et al. *Optimal antidiarrhea treatment for antitumor agent irinotecan hydrochloride (CRT-11)-induced delayed diarrhea. Cancer Chemother. Pharmacol.* 58, 494-503 (2006).

Glucuronidation represents a major route of drug detoxification in human. However, deconjugation of glucuronides by β-glucuronidase (βG) in the intestinal micro flora can induce severe toxicity during cancer chemotherapy and promote carcinogenesis for development of colorectal carcinoma. The currently used anticancer drugs such as irinotecan (CPT-11) [Kobayashi, K. *Chemotherapy-induced diarrhea. Cancer & chemotherapy* 30, 765-771 (2003)], 5-FU [Cascinu, S. et al. *High-dose loperamide in the treatment of 5-fluorouracil-induced diarrhea in colorectal cancer patients. Supportive care in cancer,* 8, 65-67 (2000)], oxaliplatin [Dranitsaris, G., et al. *Severe chemotherapy-induced diarrhea in patients with colorectal cancer: a cost of illness analysis. Supportive care in cancer,* 13, 318-324 (2005)] have been found to induce a serious side effect of chemotherapy-induced diarrhea (CID) which may lead to the reduction of administration dose or even cause the interruption of chemotherapy [Viele, C. S. *Overview of chemotherapy-induced diarrhea. Semin. Oncol. Nurs.* 19, 2-5 (2003)]. CID is a common problem, especially in patients with advanced cancers. Therefore, discovery of specific βG inhibitors in the intestinal, i.e., compounds inhibit only bacterial βG (*E. coli* βG; eβG) but not human βG (hβG) are in an urgent need.

A number of βG inhibitors have been discovered to reduce bioactivation of SN-38G and alleviate CPT-11 induced diarrhea [Benson, A. B., 3rd et al. *Recommended guidelines for the treatment of cancer treatment-induced diarrhea. J. Clin. Oncol.* 22, 2918-2926 (2004)]. For example, glucaro-1,4-lactone was found to improve CID symptom caused by the administration of CPT-11 [Takasuna, K. et al. *Optimal antidiarrhea treatment for antitumor agent irinotecan hydrochloride (CRT-11)-induced delayed diarrhea. Cancer Chemother. Pharmacol.* 58, 494-503 (2006)]. However, administration of glucaro-1,4-lactone, a non-selective βG inhibitor, may lead to the side effects of mucopolysaccharidosis symptoms due to its strong inhibitory effects against hβG [Fittkau, M., et al. *Saccharic acid 1,4-lactone protects against CPT-11-induced mucosa damage in rats. J. Cancer Res. Clin.* 130, 388-394 (2004); Constantopoulos, G., et al. *Experimental animal model for mucopolysaccharidosis: suramin-induced glycosaminoglycan and sphingolipid accumulation in the rat. Proc. Natl. Acad. Sci. USA.* 77, 3700-3704 (1980)]. In addition, literatures have also revealed that enteric eβG played an important role in the metabilic activation of glucuronide conjugated carcinogenic agents, leading to the formation of colon cancers [Kaderlik, K. R. et al. *Metabolic activation pathway for the formation of DNA adducts of the carcinogen 2-amino-1-methyl-6-phenylimidazo[4,5-b]pyridine (PhIP) in rat extrahepatic tissues. Carcinogenesis* 15, 1703-1709 (1994); Nalini, N., et al. *Effect of coconut cake on the bacterial enzyme activity in 1,2-dimethyl hydrazine induced colon cancer. Clin. Chim. Acta.* 342, 203-210 (2004); Nalini, N., et al. *Influence of spices on the bacterial (enzyme) activity in experimental colon cancer. J. Ethnopharmacol.* 62, 15-24 (1998)]. Kim et al discovered that inhibition of enteric eβG activity reduced the incident of colon cancers and the activity of eβG in colon cancer patients are 12.1 folds higher than that of normal controls [Kim, D. H. & Jin, Y. H. *Intestinal bacterial beta-glucuronidase activity of patients with colon cancer. Arch. Pharm. Res.* 24, 564-567 (2001)]. Humblot, C. et al have also proved the positive correlation of enteric eβG activity and the colonic genotoxicity [Humblot, C. et al. *Beta-glucuronidase in human intestinal microbiota is necessary for the colonic genotoxicity of the food-borne carcinogen 2-amino-3-methylimidazo [4,5-f]quinoline in rats. Carcinogenesis* 28, 2419-2425 (2007)]. Recently, 1-((6,8-Dimethyl-2-oxo-1,2-dihydroquinolin-3-yl)methyl)-3-(4-ethoxyphenyl)-1-(2-hydroxyethyl)thiourea (βG-Inh, the only published eβG specific inhibitor)

was discovered as the most potent and specific eβG inhibitor [Wallace, B. D. et al. *Alleviating cancer drug toxicity by inhibiting a bacterial enzyme. Science* 330, 831-835 (2010)]. The following figure shows the structures of glucaro-1,4-lactone and βG-Inh.

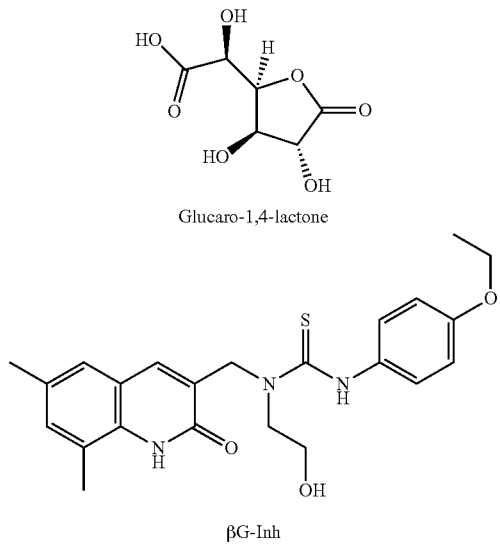

Glucaro-1,4-lactone

βG-Inh

Moreover, U.S. Pat. No. 5,447,719 provides a β-glucuronidase inhibitor comprising at least one compound selected from the group consisting of baicalin, oroxylin A-7-O-glucuronide and luteolin-3'-glucuronide; an extract of scutellaria root and/or schizonepeta spike; or a Chinese and Japanese traditional prescription comprised of scutellaria root and/or schizonepeta spike as a crude drug. US 20130345235 relates to phenoxy thiophene sulfonamides that inhibit bacterial glucuronidase and compositions including one or more of such compounds and methods of using one or more of such compounds as a co-drug to be used in combination with a camptothecin-derived anticancer drug.

However, the efficacy and specificity of βG-Inh is far from ideal and therefore, identification of more potent and selective eβG inhibitors attracted our attention.

SUMMARY OF THE INVENTION

The invention provides a compound having the following Formula I,

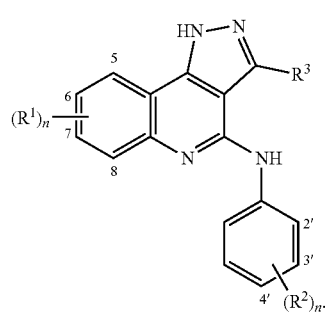

(I)

The compound of the invention can be used as (1) chemotherapy-adjuvant to prevent chemotherapy-induced diarrhea (CID) and enhance chemotherapeutic efficiency of cancers; (2) as health-food supplement to prevent the carcinogens induced colon carcinoma. Accordingly, the compounds and compositions of the invention find use as therapeutics for the treatment and/or prophylaxis of chemotherapy-induced diarrhea and carcinogens induced colon carcinoma in a subject. In further embodiment, the invention provides a method for reduction/inhibition of re-activation of a therapeutic agent metabolized through glucuronidation in a subject, comprising administering an effective amount of the compound or the composition as described herein to a subject.

BRIEF DESCRIPTION OF THE DRAWING

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
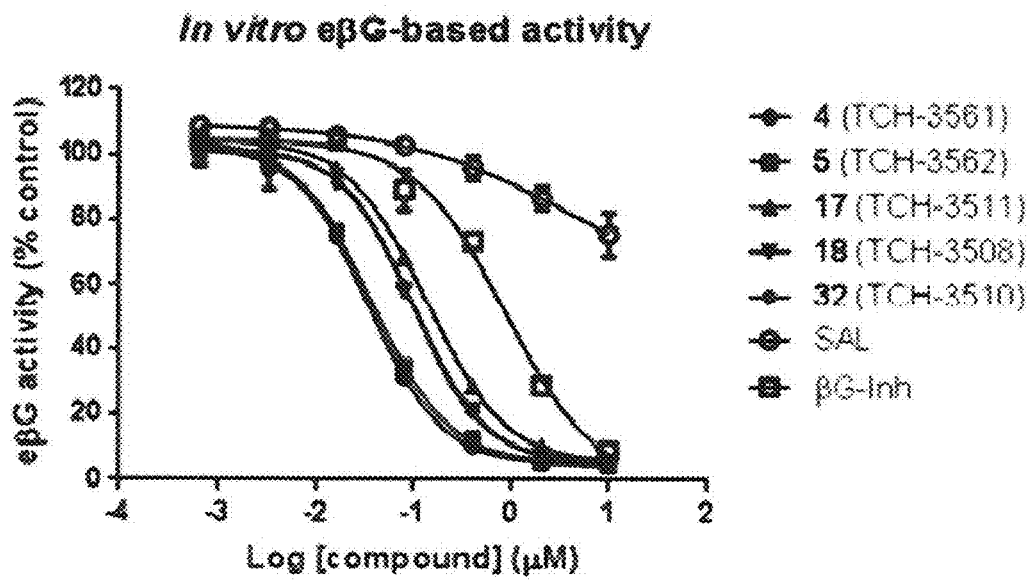
FIGS. 1A and B show selective inhibition of pyrazolo[4,3-c]quinoline derivatives. (A) inhibition against eβG; (B) inhibition against hβG.

The present invention provides novel pyrazolo[4,3-c]quinoline derivatives exhibiting specifically inhibition activity to microbiota β-glucuronidase, whereby providing potent activities to prevent chemotherapy-induced diarrhea (CID) of cancers. Therefore, the compounds of the present invention can be used as (1) chemotherapy-adjuvant to prevent chemotherapy-induced diarrhea (CID) and enhance chemotherapeutic efficiency of cancers; (2) health-food supplement to prevent the carcinogens induced colon carcinoma.

Definitions

The articles "a" and "an" may be used herein to refer to one or to more than one (i.e. at least one) of the grammatical objects of the article. By way of example "an analogue" means one analogue or more than one analogue.

As used herein, the term "comprising" means various components can be conjointly employed in the pharmaceutical composition of this invention. Accordingly, the terms "consisting essentially of" and "consisting of" are embodied in the term comprising.

As used herein, the term "substituted" refers to a group in which one or more hydrogen atoms are each independently replaced with the same or different substituent(s).

As used herein, the term "alkyl" means straight or branched aliphatic hydrocarbon having 1 to 20 carbon atoms. Particular alkyl has 1 to 8 carbon atoms. More particular is lower alkyl which has 1 to 6 carbon atoms. A further particular group has 1 to 4 carbon atoms. Exemplary straight chained groups include methyl, ethyl n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and isoamyl.

As used herein the term "alkenyl radical" denotes a linear or branched, unsaturated hydrocarbon-based chain containing from 2 to 10 carbon atoms and comprising one or more double bonds.

As used herein the term, "alkynyl radical" denotes a linear or branched, unsaturated hydrocarbon-based chain containing from 2 to 10 carbon atoms and comprising one or more triple bonds.

As used herein, the term "cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

As used herein the term "aryl" denotes an aromatic hydrocarbon-based ring or two fused aromatic hydrocarbon-based rings. The preferred aryl is phenyl of naphthyl.

As used herein, the term "alkoxy" refers to straight or branched chain alkoxides of the number of carbon atoms specified (e.g., $C_{1-10}$alkoxy), or any number within this range (i.e., methoxy (MeO—), ethoxy, isopropoxy, etc.)

As used herein, the term "alkylthio" refers to straight or branched chain alkylsulfides of the number of carbon atoms specified (e.g., $C_{1-10}$alkylthio), or any number within this range (i.e., methylthio (MeS—), ethylthio, isopropylthio, etc.)

As used herein, the term "alkylamino" refers to straight or branched alkylamines of the number of carbon atoms specified (e.g., $C_{1-10}$alkylamino), or any number within this range (i.e., methylamino, ethylamino, isopropylamino, t-butylamino, etc.)

As used herein, the term "heteroaryl" refers to a group having from 5 to 14 ring atoms; 6, 10 or 14 pi electrons shared in a cyclic array; and containing carbon atoms and 1, 2 or 3 oxygen, nitrogen and/or sulfur heteroatoms. Examples of heteroaryl groups include indazolyl, furyl, thienyl, pyrrolyl, imidazolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, tetrazolyl, triazinyl, azepinyl, oxazepinyl, morpholinyl, thiazepinyl, diazepinyl, thiazolinyl, benzimidazolyl, benzoxazolyl, imidazopyridinyl, benzoxazinyl, benzothiazinyl, benzothiophenyl oxazolopyridinyl, benzofuranyl, quinolinyl, quinazolinyl, quinoxalinyl, benzothiazolyl, phthalimido, benzofuranyl, benzodiazepinyl, indolyl, indanyl, azaindazolyl, deazapurinyl and isoindolyl.

As used herein, the term "pharmaceutically acceptable salt" refers to any salt of a compound of this invention which retains its biological properties and which is not toxic or otherwise undesirable for pharmaceutical use. Such salts may be derived from a variety of organic and inorganic counter-ions well known in the art and include.

As used herein, the term "solvate" refers to a compound of the present invention or a salt thereof that further includes a stoichiometric or non-stoichiometric amount of solvent bound by non-covalent intermolecular forces. Where the solvent is water, the solvate is a hydrate.

As used herein, the term "prodrug" refers to compounds, including derivatives of the compound of the invention, which have cleavable groups and become by solvolysis or under physiological conditions the compound of the invention which are pharmaceutically active in vivo. Such examples include, but are not limited to, choline ester derivatives and the like, N-alkylmorpholine esters and the like.

As used herein, the terms "disorder," "condition" and "disease" are used interchangeably to refer to a condition in a subject. Certain conditions may be characterized as more than one disorder.

As used herein, the term "effective amount" means the amount of a compound for alleviating a disease or a condition. The term "therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

As used herein, the terms "prevent," "preventing" and "prevention" refer to the prevention of the recurrence, onset, or development of one or more symptoms of a disorder in a subject resulting from the administration of a therapy, or the administration of a combination of therapies.

As used herein, the terms "treat", "treatment" and "treating" refer to the reduction or amelioration of the progression, severity and/or duration of a disorder, or the amelioration of one or more symptoms thereof resulting from the administration of one or more therapies.

As used herein, the terms "subject" and "patient" are used interchangeably herein. The terms "subject" and "subjects" refer to an animal, in certain embodiments a mammal including a non-primate (e.g., a cow, pig, horse, cat, dog, rat, and mouse) and a primate (e.g., a monkey such as a cynomolgous monkey, a chimpanzee and a human), and more particularly a human. In certain embodiments, the subject is a human.

Compounds of the Present Invention

In one aspect, the present invention provides a compound having the following Formula I,

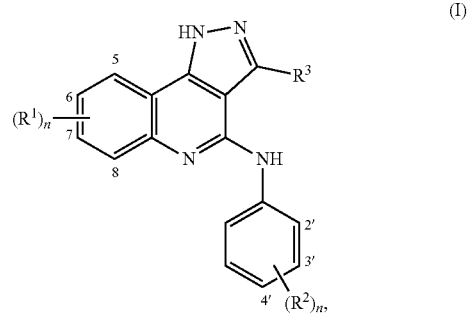

(I)

wherein n represents 0 to 4 substituents;

$R^1$ represents 1 to 4 substituents; each $R^1$ is independently H, halogen, OH, CN, $NH_2$, $NO_2$, alkyl, alkenyl, alkynyl, alkoxy, haloalkyl, unsubstituted or substituted cycloalkyl, unsubstituted or substituted aryl or unsubstituted or substituted heteroaryl;

$R^2$ is H, halogen, alkyl, alkoxy, alkylthio, alkylamino, OH, CN, $NH_2$, $NO_2$, $OR^4$, $SR^4$, $COR^5$, $COOR^6$, alkenyl, alkynyl, haloalkyl, unsubstituted or substituted cycloalkyl, unsubstituted or substituted aryl or unsubstituted or substituted heteroaryl;

$R^3$ is halogen, CN, OH, $NO_2$, $NR^aR^b$, alkyl, alkenyl, alkynyl, alkoxy, haloalkyl, cycloalkyl, unsubstituted or substituted aryl or unsubstituted or substituted heteroaryl;

$R^4$ is halogen, CN, OH, $NH_2$, $NO_2$, alkyl, alkenyl, alkynyl, alkoxy, haloalkyl, unsubstituted or substituted cycloalkyl, unsubstituted or substituted aryl or unsubstituted or substituted heteroaryl;

$R^5$ and $R^6$ are each independently H, halogen, CN, OH, $NH_2$, $NO_2$, alkyl, alkenyl, alkynyl, alkoxy, haloalkyl, unsubstituted or substituted cycloalkyl, unsubstituted or substituted aryl or unsubstituted or substituted heteroaryl;

$R^a$ and $R^b$ are each independently $C(O)NR^cR^d$, H, halogen, OH, CN, $NH_2$, $NO_2$, alkyl, alkenyl, alkynyl, alkoxy, haloalkyl, unsubstituted or substituted cycloalkyl, unsubstituted or substituted aryl or unsubstituted or substituted heteroaryl; and $R^c$ and $R^d$ are each independently H, halogen, CN, OH, $NH_2$, $NO_2$, alkyl, alkenyl, alkynyl, alkoxy, haloalkyl, unsubstituted or substituted cycloalkyl, unsubstituted or substituted aryl or unsubstituted or substituted heteroaryl;

or an isomer, a pharmaceutical acceptable salt, prodrug or solvate thereof.

In some embodiments, each of cycloalkyl, aryl and heteroaryl is unsubstituted or substituted by halogen, CN, OH, $NH_2$, $NO_2$, alkyl, alkenyl, alkynyl, alkoxy, haloalkyl, unsubstituted or substituted cycloalkyl, unsubstituted or substituted aryl or unsubstituted or substituted heteroaryl.

In some embodiments, heteroaryl is $C_{6-10}$ membered ring and has one to three hetero atoms selected from N, O and S.

In some embodiments, $R^1$ is H, halogen or $C_{1-10}$alkyl substituted at C-5, C-6, C-7 or C-8 position. In a further embodiment, $R^1$ is H, halogen or $C_{1-4}$alkyl. In a further embodiment, R1 is H, Cl, F, Br, methyl. In a further embodiment, $R^1$ is H.

In some embodiments, $R^2$ is H, halogen, $C_{1-10}$alkyl, $C_{1-10}$alkoxy, $C_{1-10}$alkylthio, $NH_2$, $NO_2$, haloalkyl, $COR^5$, or $COOR^5$ substituted at C-2', C-3' or C-4' position. In a further embodiment, $R^2$ is H, halogen, $C_{1-4}$alkyl, $C_{1-4}$alkoxy, $C_{1-4}$alkylthio, $NH_2$, $NO_2$, halo$C_{1-4}$alkyl, $C(O)C_{1-4}$alkyl, or COOH. In a further embodiment, $R^2$ is H, methyl, OH, $NH_2$, methoxy, methylthio, $CF_3$, Cl, F, $NO_2$, COOH, $C(O)CH_3$.

In some embodiments, $R^3$ is $NR^aR^b$, OH or $NO_2$, wherein $R^a$ and $R^b$ are each independently H or $C(O)NR^cR^d$ and $R^c$ and $R^d$ are each independently H or unsubstituted or substituted aryl. In some embodiments, aryl are unsubstituted or substituted by $C_{1-6}$alkoxy; preferably —$OCH_3$. Preferably, $R^3$ is $NH_2$, OH, $NO_2$, phenyl, phenyl substituted by —$OCH_3$.

In some embodiments, the compound of the invention has one of the following formulae:

Formula I

Formula II wherein $R^1$ and $R^2$ has the definitions as mentioned above and R is H or one to t4 halogen, CN, OH, $NH_2$, $NO_2$, alkyl, alkenyl, alkynyl, alkoxy, haloalkyl, unsubstituted or substituted cycloalkyl, unsubstituted or substituted aryl or unsubstituted or substituted heteroaryl.

In a further embodiment, the compound of the invention is selected from the group consisting of:
4-Hydroxy-8-methyl-2-oxo-1,2-dihydroquinoline-3-carbonitrile;
2,6-Bromo-4-hydroxy-2-oxo-1,2-dihydroquinoline-3-carbonitrile;
2,4-Dichloro-8-methylquinoline-3-carbonitrile;
4,6-Bromo-2,4-dichloroquinoline-3-carbonitrile;
4-Chloro-6-methyl-1H-pyrazolo[4,3-c]quinolin-3-amine;
4-Chloro-7-fluoro-1H-pyrazolo[4,3-c]quinolin-3-amine;
4,8-Dichloro-1H-pyrazolo[4,3-c]quinolin-3-amine;
8-Bromo-4-chloro-1H-pyrazolo[4,3-c]quinolin-3-amine;
3-Amino-4-(4-chlorophenylamino)-1H-pyrazolo[4,3-c]quinoline;
3-Amino-4-(4-methylphenylamino)-1H-pyrazolo[4,3-c]quinoline;
$N^4$-(4-Chlorophenyl)-6-methyl-1H-pyrazolo[4,3-c]quinoline-3,4-diamine;
6-Methyl-$N^4$-(p-tolyl)-1H-pyrazolo[4,3-c]quinoline-3,4-diamine;
$N^4$-(4-Chlorophenyl)-7-fluoro-1H-pyrazolo[4,3-c]quinoline-3,4-diamine;
7-Fluoro-$N^4$-(p-tolyl)-1H-pyrazolo[4,3-c]quinoline-3,4-diamine;
8-Chloro-$N^4$-(4-chlorophenyl)-1H-pyrazolo[4,3-c]quinoline-3,4-diamine;
8-Chloro-$N^4$-(p-tolyl)-1H-pyrazolo[4,3-c]quinoline-3,4-diamine;
8-Bromo-$N^4$-(4-chlorophenyl)-1H-pyrazolo[4,3-c]quinoline-3,4-diamine;
8-Bromo-$N^4$-(p-tolyl)-1H-pyrazolo[4,3-c]quinoline-3,4-diamine;

3-Amino-4-anilino-1H-pyrazolo[4,3-c]quinoline;
3-Amino-4-(4-hydroxyphenylamino)-1H-pyrazolo[4,3-c]quinoline;
3-Amino-4-(4-aminophenylamino)-1H-pyrazolo[4,3-c]quinoline;
3-Amino-4-(4-fluorophenylamino)-1H-pyrazolo[4,3-c]quinoline;
3-Amino-4-(4-trifluoromethylphenylamino)-1H-pyrazolo[4,3-c]quinoline;
3-Amino-4-(4-methoxyphenylamino)-1H-pyrazolo[4,3-c]quinoline;
3-Amino-4-(4-methylthiophenylamino)-1H-pyrazolo[4,3-c]quinoline;
3-Amino-4-(4-nitrophenylamino)-1H-pyrazolo[4,3-c]quinoline;
4-(3-Amino-1H-pyrazolo[4,3-c]quinolin-4-ylamino)benzoic acid;
3-Amino-4-(4-acetylphenylamino)-1H-pyrazolo[4,3-c]quinoline;
3-Amino-4-(3-hydroxyphenylamino)-1H-pyrazolo[4,3-c]quinoline;
$N^4$-(m-Tolyl)-1H-pyrazolo[4,3-c]quinoline-3,4-diamine;
$N^4$-(3-Chlorophenyl)-1H-pyrazolo[4,3-c]-quinoline-3,4-diamine;
3-Amino-4-(3-methoxyphenylamino)-1H-pyrazolo[4,3-c]quinoline;
3-Amino-4-(3-acetylphenylamino)-1H-pyrazolo[4,3-c]quinoline;
3-Amino-4-(2-hydroxyphenylamino)-1H-pyrazolo[4,3-c]quinoline;
$N^4$-(o-Tolyl)-1H-pyrazolo[4,3-c]quinoline-3,4-diamine;
$N^4$-(2-Chlorophenyl)-1H-pyrazolo[4,3-c]quinoline-3,4-diamine;
3-Amino-4-(2-methoxyphenylamino)-1H-pyrazolo[4,3-c]quinoline;
3-Amino-1H-pyrazolo[4,3-c]quinolin-4(5H)-one;
1-(4-oxo-4,5-dihydro-1H-pyrazolo[4,3-c]quinolin-3-yl)-3-phenylurea;
1-(4-Methoxyphenyl)-3-(4-oxo-4,5-dihydro-1H-pyrazolo[4,3-c]-quinolin-3-yl)urea;
1-{4-[(4-Chlorophenyl)amino]-1H-pyrazolo[4,3-c]quinolin-3-yl}-3-phenylurea;
1-Phenyl-3-[4-(p-tolylamino)-1H-pyrazolo[4,3-c]quinolin-3-yl]urea;
1-{4-[(4-Chlorophenyl)amino]-1H-pyrazolo[4,3-c]quinolin-3-yl}-3-(4-methoxyphenyl)urea; and
1-(4-Methoxyphenyl)-3-[4-(p-tolylamino)-1H-pyrazolo[4,3-c]-quinolin-3-yl]urea;
or an isomer, a pharmaceutical acceptable salt, prodrug or solvate thereof.

In another further embodiment, the compound of the invention is selected from the group consisting of:

TCH-3510
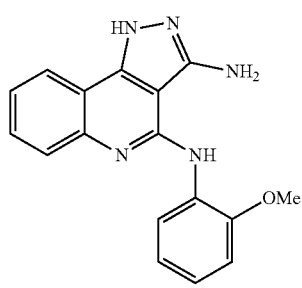

TCH-3511
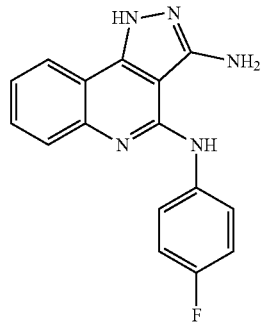

TCH-3561
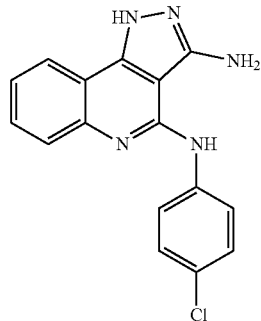

TCH-3562
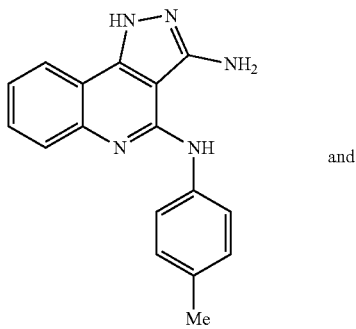

and

TCH-3508
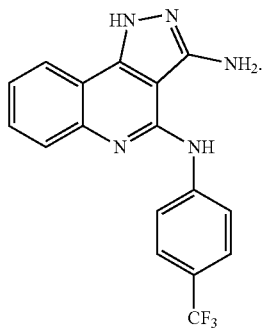

It is to be understood that compounds having the same molecular formula but differing in the nature or sequence of bonding of their atoms or in the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, when it is bonded to four different groups, a pair of enantiomers is possible. An enantiomer can be characterized by the absolute configuration of its asymmetric center and is designated (R) or (S) according to the rules of Cahn and Prelog (Mata and Lobo, 1993, Tetrahedron: Asymmetry 4:657-668) or can be characterized by the manner in which the molecule rotates the plane of polarized light and is designated dextrorotatory or levorotatory (i.e., as (+)- or (−)-isomers, respectively). A chiral compound can exist as either individual enantiomer or as a mixture thereof. A mixture containing equal proportions of enantiomers is called a "racemic mixture".

In one embodiment, the pharmaceutical salts of the compounds described herein include but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like. Salts further include, by way of example only, sodium, potassium, calcium, magnesium, ammonium, tetraalkylammonium and the like, and when the compound contains a basic functionality, salts of non-toxic organic or inorganic acids, such as hydrochloride, hydrobromide, tartrate, mesylate, besylate, acetate, maleate, oxalate and the like. The term "physiologically acceptable cation" refers to a non-toxic, physiologically acceptable cationic counterion of an acidic functional group. Such cations are exemplified by sodium, potassium, calcium, magnesium, ammonium and tetraalkylammonium cations and the like.

Preparation of the Compounds of the Invention

These pyrazolo[4,3-c]quinoline derivatives can be prepared according to the protocols as following reaction scheme (Scheme 1). Treatment of 4-hydroxy-2-oxo-1,2-dihydroquinoline-3-carbonitriles (1) with POCl3 afforded 2,4-dichloroquinoline-3-carbonitriles (2) which were then reacted with hydrazine to give 4-chloro-1H-pyrazolo[4,3-c]quinohn-3-amines (3). Reaction of compound 3 with substituted aniline produced 3-amino-4-substituted anilino-1H-pyrazolo[4,3-c]quinolines (4-32).

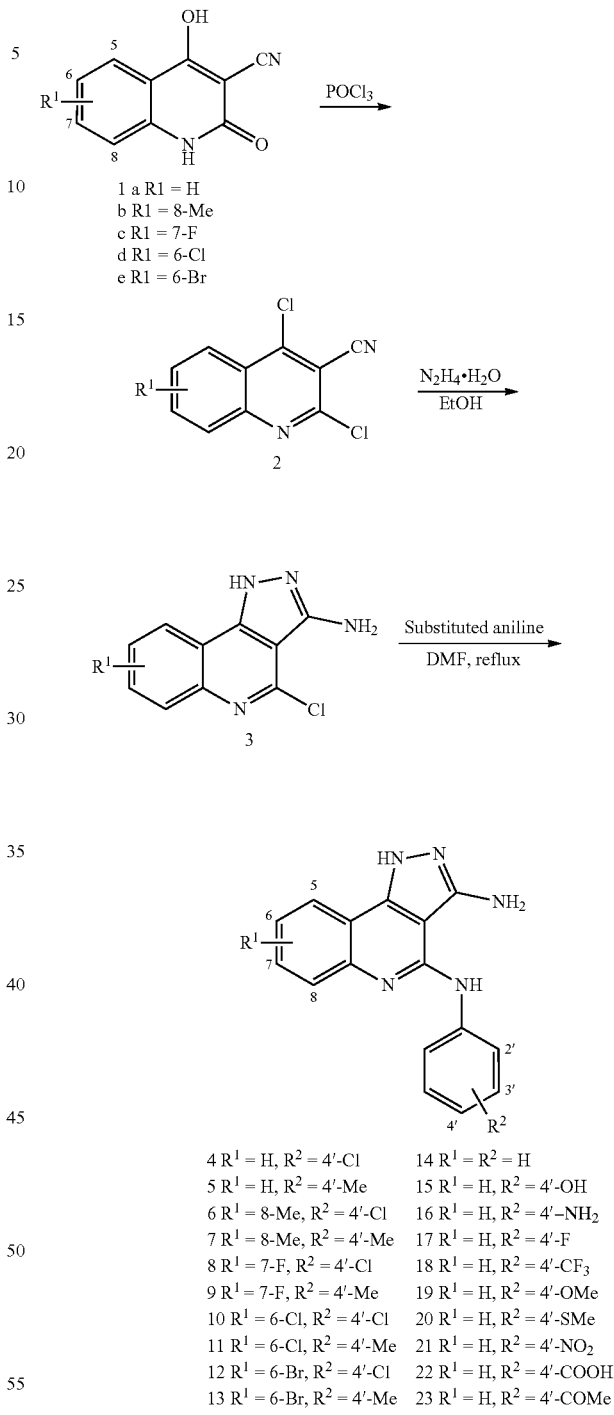

Scheme 1

Scheme 2

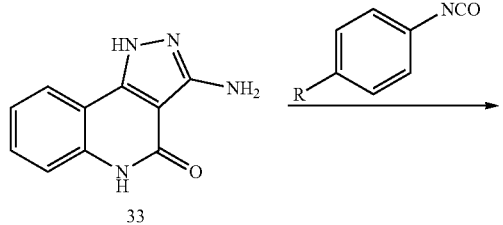

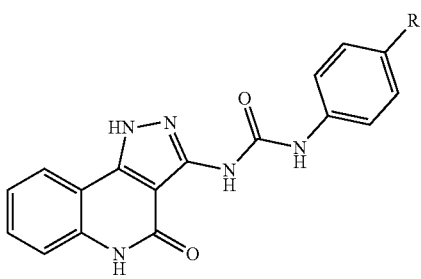

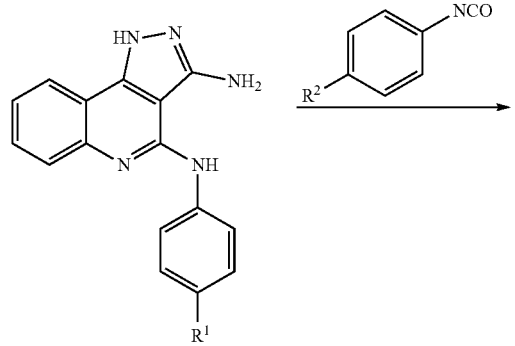

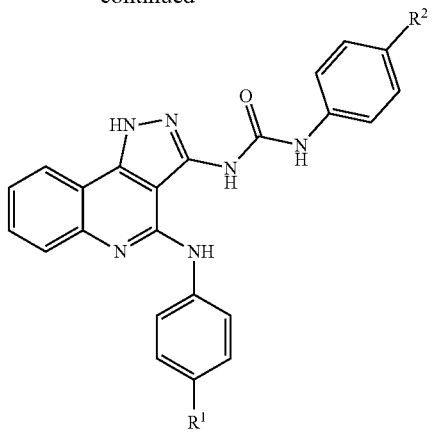

36 R¹ = Cl, R² = H
37 R¹ = Me, R² = H
38 R¹ = Cl, R² = OMe
39 R¹ = Me, R² = OMe

Compositions Comprising the Compounds of the Present Invention

When employed as a pharmaceutical or a food supplement, the compound of the invention is typically administered in the form of a pharmaceutical or food composition. Such compositions can be prepared in a manner well known in the pharmaceutical or food art and comprise at least one active compound. Generally, the compound of this invention is administered in an effective amount of a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical or food compositions of the invention can be administered by a variety of routes including oral, rectal, subcutaneous, intra-articular, intravenous and intramuscular. Depending on the intended route of delivery, a compound of this invention is preferably formulated as either injectable or oral compositions or as salves, as lotions or as patches all for transdermal administration.

For oral administration, a compound of the present teachings may be incorporated with excipient and used in the form of ingestible tablets, buccal tablets, troches, capsules, elixirs, suspensions, syrups, wafers, and the like. The compositions for oral administration can take the form of bulk liquid solutions or suspensions, or bulk powders. More commonly, however, the compositions are presented in unit dosage forms to facilitate accurate dosing. The term "unit dosage form" refers to physically discrete units suitable as unitary dosages for human subjects and other mammals, each unit containing a predetermined quantity of active material calculated to produce the desired therapeutic effect, in association with a suitable excipient, vehicle or carrier. Typical unit dosage forms include prefilled, premeasured ampules or syringes of the liquid compositions or pills, tablets, capsules or the like in the case of solid compositions. In such compositions, the compound of the invention is usually a minor component (e.g., 1-6 mg/kg/day) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art.

For rectal administration, the compounds described herein can be formulated in the form of suppositories containing a conventional suppository base such as cocoa butter.

The composition of the present invention can comprise an additional therapeutic agent. In one embodiment, the therapeutic agent can be any agent metabolized through glucuronidation. In some embodiments, an therapeutic agent is an anti-cancer agent, an immunopotentiator or an immunomodulator. For example, the anti-cancer agent includes but is not limited to tamoxifen, toremifene, raloxifene, droloxifene, iodoxyfene, megestrol acetate, anastrozole, letrazole, borazole, exemestane, flutamide, nilutamide, bicalutamide, cyproterone acetate, goserelin acetate, luprolide, finasteride, herceptin, methotrexate, 5-fluorouracil, cytosine arabinoside, doxorubicin, daunomycin, epirubicin, idarubicin, mitomycin-C, dactinomycin, mithramycin, cisplatin, carboplatin, melphalan, chlorambucil, busulphan, cyclophosphamide, ifosfamide, nitrosoureas, thiotephan, vincristine, taxol, taxotere, etoposide, teniposide, amsacrine, irinotecan, topotecan, an epothilone, and the like.

Administrations of the Compounds/Compositions of the Present Invention

The compound of the invention may be used as (1) chemotherapy-adjuvant to prevent chemotherapy-induced diarrhea (CID) and enhance chemotherapeutic efficiency of cancers; (2) health-food supplement to prevent the carcinogens induced colon carcinoma.

Accordingly, the compounds and compositions of the invention find use as therapeutics for the treatment or prophylaxis of chemotherapy-induced diarrhea and carcinogens induced colon carcinoma in a subject.

In one aspect, the present invention provides the compound of the invention, or a composition comprising the compound of the invention for use as a medicament.

In one embodiment, the invention provides a method for selectively inhibiting microbiota βG but not human βG (hβG), comprising administering an effective amount of the compound of the invention to a subject.

In one embodiment, the invention provides a method for reduction/inhibition of re-activation of a therapeutic agent metabolized through glucuronidation in a subject, comprising administering an effective amount of the compound of the invention or the composition of the invention to a subject.

In another embodiment, the invention provides a method for treatment or prophylaxis of chemotherapy-induced diarrhea or carcinogens induced colon carcinoma in a subject, comprising administering an effective amount of the compound of the invention to a subject.

In a further embodiment, the invention provides a method for enhancing chemotherapeutic efficiency of cancers, comprising administering an effective amount of the compound of the invention to a subject.

As a further aspect of the invention there is provided the compound of the invention for use as a pharmaceutical or food in the treatment or prophylaxis of the aforementioned conditions and diseases. Also provided herein is the use of the present compounds in the manufacture of a medicament or food preparation for the treatment or prophylaxis of one of the aforementioned conditions and diseases.

A particular regimen of the present method comprises the administration to a subject suffering from a disease involving chemotherapy-induced diarrhea (CID) or the carcinogens induced colon carcinoma; or the administration to a subject to enhance chemotherapeutic efficiency of cancers.

A further particular regimen of the present method comprises the administration to a subject receiving one or more treatments such as angiogenic inhibitors, chemotherapy, radiation, surgery, or other treatments known to those of skill in the art to prevent and/or treat cancer. A particular embodiment of the method comprises administering of an effective amount of the compound of the invention to a subject chemotherapy-induced diarrhea (CID) or the carcinogens induced colon carcinoma. Another particular embodiment of the method comprises administering of an effective amount of the compound of the invention to a subject to enhance chemotherapeutic efficiency of a cancer. In a particular embodiment, the dose level range from about 1 to about 6 mg/kg/day.

When used to prevent the onset of a condition, the compound of the invention will be administered to a patient at risk for developing the condition, typically on the advice and under the supervision of a physician, at the dosage levels described above.

The compound of the invention can be administered as the sole active agent or it can be administered in combination with other therapeutic agents, preferably any agent metabolized through glucuronidation, including an anti-cancer agent, an immunopotentiator or an immunomodulator. In a specific embodiment, co-administration of two (or more) agents can be used.

In one embodiment, the compound of the invention is co-administered with an anti-cancer agent for the treatment and/or prophylaxis of a cancer, particular agents include but are not limited to the anti-cancer drug metabolized through glucuronidation. Additionally, the compound of the invention may be administered in combination with other therapies including, but not limited to, radiotherapy, chemotherapy or surgery.

By co-administration is included any means of delivering two or more therapeutic agents to the patient as part of the same treatment regime, as will be apparent to the skilled person. Whilst the two or more agents may be administered simultaneously in a single formulation, i.e. as a single pharmaceutical composition, this is not essential. The agents may be administered separately in different formulations and at different times.

EXAMPLE

Example 1 General Preparation Process

General. TLC: precoated (0.2 mm) silica gel 60 $F_{254}$ plates from EM Laboratories, Inc.; detection by UV light (254 nm). M.p.: Electrothermal IA9100 digital melting-point apparatus; uncorrected. $^1$H and $^{13}$C NMR spectra: Varian-Unity-400 spectrometer at 400 and 100 MHz or Varian-Gemini-200 spectrometer at 200 and 50 MHz, chemical shifts δ in ppm with SiMe$_4$ as an internal standard (=0 ppm), coupling constants J in Hz. Elemental analyses were carried out on a Heraeus CHN-O-Rapid elemental analyzer, and results were within ±0.4% of calculated values.

Example 2 4-Hydroxy-8-methyl-2-oxo-1,2-dihydro-quinoline-3-carbonitrile 1b ($R^1$=8-Me)

A mixture of 8-methylisatoic anhydride (3.46 g, 19.5 mmol), ethyl cyanoacetate (2.21 g, 19.5 mmol) and Et3N (3 mL, 20 mmol) in DMF (15 mL) was heated at 160° C. for 18 h (TLC monitoring). The reaction mixture was concentrated in vacuo followed by the addition of 1N HCl. Precipitate was collected by filtration, washed with H$_2$O and dried to yield brown solid. The crude product was recrystallized with MeOH to give 1b (2.00 g, 51%). Mp.: 276-277° C. $^1$H-NMR (400 MHz, DMSO-d$_6$): 2.40 (s, 3H, 8-Me), 7.15 (dd, 1H, J=7.2, 7.6 Hz, 6-H), 7.49 (d, 1H, J=7.2 Hz, 7-H), 7.88 (d, 1H, J=7.6 Hz, 5-H), 10.88 (br s, 1H, NH).

Example 3 6-Bromo-4-hydroxy-2-oxo-1,2-dihydro-quinoline-3-carbonitrile 1e ($R^1$=6-Br)

Yield 95%. Mp.: 280-282° C. $^1$H-NMR (200 MHz, DMSO-d$_6$): 7.23 (d, 1H, J=8.8 Hz, 8-H), 7.63 (dd, 1H, J=8.8, 2.2 Hz, 7-H), 8.13 (d, 1H, J=2.2 Hz, 5-H), 11.73 (br s, 1H, NH).

Example 4
2,4-Dichloro-8-methylquinoline-3-carbonitrile 2b ($R^1$=8-Me)

A mixture of 1b (1.99 g, 10 mmol) in POCl$_3$ (30 mL) was heated at 140° C. for 3 h (TLC monitoring). After cooling, the mixture was poured into ice-water (50 mL) and neutralized with saturated Na$_2$CO$_3$ until pH 7 resulted. This aqueous mixture was extracted with CH$_2$Cl$_2$ (50 mL×3), dried (MgSO$_4$), and concentrated to yield brown solid. The crude product was purified by FC (using n-hexane:CH$_2$Cl$_2$=1:2 as the eluent) to give a white solid, which was recrystallized with MeOH to give 2b (1.50 g, 64%). Mp.: 156-158° C. $^1$H-NMR (200 MHz, DMSO-d$_6$): 2.67 (s, 3H, 8-Me), 7.80 (dd, 1H, J=6.4, 8.4 Hz, 6-H), 7.97 (d, 1H, J=6.4 Hz, 7-H), 8.07 (d, 1H, J=8.4 Hz, 5-H).

Example 5
6-Bromo-2,4-dichloroquinoline-3-carbonitrile 2e ($R^1$=6-Br)

Yield 65%. Mp.: 191-193° C. $^1$H-NMR (200 MHz, DMSO-d$_6$): 8.05 (d, 1H, J=9.0 Hz, 8-H), 8.23 (dd, 1H, J=9.0, 2.2 Hz, 7-H), 8.44 (d, 1H, J=2.2 Hz, 5-H).

Example 6 4-Chloro-6-methyl-1H-pyrazolo[4,3-c]quinolin-3-amine 3b ($R^1$=8-Me)

A mixture of 2b (1.17 g, 5 mmol) in hydraize hydrate (20 mL) and EtOH (30 mL) was heated at 60° C. for 10 min (TLC monitoring). The reaction mixture was concentrated in vacuo followed by the addition of H$_2$O (100 mL). Precipitate was collected by filtration, washed with H$_2$O and dried to yield white solid. The crude product was recrystallized with MeOH to give 3b (0.98 g, 84%). Mp.: 216-217° C. $^1$H-NMR (400 MHz, DMSO-d$_6$): 2.66 (s, 3H, 8-Me), 5.63 (br s, 2H, NH$_2$), 7.53-7.60 (m, 2H, Ar—H), 8.10 (d, 1H, J=7.6 Hz, Ar—H), 13.24 (br s, 1H, NH).

Example 7 4-Chloro-7-fluoro-1H-pyrazolo[4,3-c]quinolin-3-amine 3d ($R^1$=7-F)

Yield 72%. Mp.: 224° C. (dec.) $^1$H-NMR (200 MHz, DMSO-d$_6$): 5.84 (br s, 2H, NH$_2$), 7.57 (m, 1H, Ar—H), 7.69 (dd, 1H, J=10.4, 2.4 Hz, Ar—H), 8.30 (dd, 1H, J=8.8, 6.0 Hz, Ar—H), 13.20 (brs, 1H, NH).

Example 8 4,8-Dichloro-1H-pyrazolo[4,3-c]quinolin-3-amine 3d ($R^1$=6-Cl)

Yield 90%. Mp.: 282° C. (dec.) $^1$H-NMR (200 MHz, DMSO-d$_6$): 5.70 (br s, 2H, NH$_2$), 7.73 (d, 1H, J=7.2 Hz, Ar—H), 7.93 (d, 1H, J=9.0 Hz, Ar—H), 8.34 (s, 1H, Ar—H), 13.28 (br s, 1H, NH).

Example 9 8-Bromo-4-chloro-1H-pyrazolo[4,3-c]quinolin-3-amine 3e ($R^1$=6-Br)

Yield 90%. Mp.: 325° C. (dec.) $^1$H-NMR (200 MHz, DMSO-d$_6$): 5.70 (br s, 2H, NH$_2$), 7.84 (s, 2H, Ar—H), 8.50 (s, 1H, Ar—H), 13.27 (br s, 1H, NH).

Example 10 General Procedure for the synthesis of 3-Amino-4-substituted anilino-1H-pyrazolo[4,3-c]quinoline 4-32

A mixture of 4-chloro-1H-pyrazolo[4,3-c]quinolin-3-amine 3a (0.44 g, 2 mmol) and appropriate aromatic amine (4 mmol) in DMF (20 mL) was refluxed with stirring for 3 hrs (by TLC monitoring). The mixture was then cooled and evaporated in vacuo to give a residue which was treated with H$_2$O (50 mL). The precipitate thus collected was washed with H$_2$O and then dried to give a crude solid, which was recrystallized from EtOH.

Example 11 3-Amino-4-(4-chlorophenylamino)-1H-pyrazolo[4,3-c]quinoline 4 ($R^1$=H, $R^2$=4'-Cl) (3561)

Yield 75%. Mp.: 246-248° C. $^1$H-NMR (400 MHz, DMSO-d$_6$): 5.62 (br s, 2H, NH$_2$), 7.26-7.30 (m, 1H, Ar—H), 7.35 (d, 2H, J=8.8 Hz, Ar—H), 7.46-7.50 (m, 1H, Ar—H), 7.61 (d, 1H, J=8.0 Hz, Ar—H), 7.99-8.05 (m, 3H, Ar—H), 8.31 (brs, 1H, NH), 12.92 (brs, 1H, NH). Anal. calcd for C$_{16}$H$_{12}$ClN$_5$.0.2H$_2$O: C, 61.33, H, 3.99, N, 22.35; found: C, 61.45, H, 3.86, N, 22.67.

Example 12 3-Amino-4-(4-methylphenylamino)-1H-pyrazolo[4,3-c]quinoline 5 ($R^1$=H, $R^2$=4'-Me) (3562)

Yield 81%. Mp.: 292-294° C. (lit. 296-298° C.)$^{28}$. $^1$H-NMR (400 MHz, DMSO-d$_6$): 2.30 (s, 3H, Me), 5.62 (br s, 2H, NH$_2$), 7.16 (d, 2H, J=8.4 Hz, Ar—H), 7.26-7.29 (m, 1H, Ar—H), 7.47-7.51 (m, 1H, Ar—H), 7.60 (d, 1H, J=8.4 Hz, Ar—H), 7.84 (d, 2H, J=8.4 Hz, Ar—H), 8.05 (d, 1H, J=8.0 Hz), 8.15 (s, 1H, NH), 12.89 (br s, 1H, NH).

Example 13 N$^4$-(4-Chlorophenyl)-6-methyl-1H-pyrazolo[4,3-c]quinoline-3,4-diamine 6 ($R^1$=8-Me, $R^2$=4'-Cl)

Yield: 83%. mp: 249-250° C. $^1$H-NMR (400 MHz, DMSO-d$_6$): 2.61 (s, 3H, Me), 5.67 (br s, 2H, NH$_2$), 7.20-

7.24 (m, 1H, Ar—H), 7.39-7.43 (m, 3H, Ar—H), 7.94 (d, 1H, J=7.6 Hz, Ar—H), 8.11 (d, 2H, J=8.8 Hz, Ar—H), 8.37 (br s, 1H, NH), 12.90 (br s, 1H, NH).

Example 14 6-Methyl-$N^4$-(p-tolyl)-1H-pyrazolo[4,3-c]quinoline-3,4-diamine 7 ($R^1$=8-Me, $R^2$=4'-Me)

Yield: 81%. mp: 270-271° C. $^1$H-NMR (400 MHz, DMSO-$d_6$): 2.29 (s, 3H, Me), 2.60 (s, 3H, Me), 5.65 (br s, 2H, $NH_2$), 7.15-7.19 (m, 3H, Ar—H), 7.39 (d, 1H, J=6.8 Hz, Ar—H), 7.90-7.97 (m, 3H, Ar—H), 8.18 (s, 1H, NH), 12.85 (br s, 1H, NH). Anal. calcd. for $C_{18}H_{17}N_5$: C, 71.67; H, 5.65; N, 23.09. Found: C, 71.21; H, 5.69; N, 23.00.

Example 15 $N^4$-(4-Chlorophenyl)-7-fluoro-1H-pyrazolo[4,3-c]quinoline-3,4-diamine 8 ($R^1$=7-F, $R^2$=4'-Cl)

Yield: 52%. mp: 254° C. (dec.). $^1$H-NMR (400 MHz, DMSO-$d_6$): 5.70 (br s, 2H, $NH_2$), 7.21 (br m, 1H, Ar—H), 7.35-7.42 (m, 3H, Ar—H), 8.00 (d, 2H, J=8.4 Hz, Ar—H), 8.09-8.14 (m, 1H, Ar—H), 8.42 (br s, 1H, NH), 12.97 (br s, 1H, NH). Anal. calcd. for $C_{16}H_{11}ClFN_5$: C, 58.63; H, 3.38; N, 21.37. Found: C, 58.72; H, 3.45; N, 21.45.

Example 16 7-Fluoro-$N^4$-(p-tolyl)-1H-pyrazolo[4,3-c]quinoline-3,4-diamine 9 ($R^1$=7-F, $R^2$=4'-Me)

Yield: 81%. mp: 246-247° C. $^1$H-NMR (400 MHZ, DMSO-$d_6$): 2.30 (s, 3H, Me), 5.68 (br s, 2H, $NH_2$), 7.14-7.17 (m, 3H, Ar—H), 7.29 (dd, 1H, J=11.2, 2.4 Hz, Ar—H), 7.80 (d, 2H, J=8.0 Hz, Ar—H), 8.08 (dd, 1H, J=8.4, 6.8 Hz, Ar—H), 8.22 (br s, 1H, NH), 12.85 (br s, 1H, NH). Anal, calcd. for $C_{17}H_{14}FN_5$. 1HCl: C, 59.37; H, 4.40; N, 20.37. Found: C, 59.31; H, 4.27; N, 20.36.

Example 17 8-Chloro-$N^4$-(4-chlorophenyl)-1H-pyrazolo[4,3-c]quinoline-3,4-diamine 10 ($R^1$=6-Cl, $R^2$=4'-Cl)

Yield: 33%. mp: 270-272° C. $^1$H-NMR (400 MHz, DMSO-$d_6$): 5.72 (br s, 2H, $NH_2$), 7.40 (d, 2H, J=8.8 Hz, Ar—H), 7.51 (d, 1H, J=8.4 Hz, Ar—H), 7.64 (d, 1H, J=8.4 Hz, Ar—H), 8.00 (d, 2H, J=8.0 Hz, Ar—H), 8.15 (s, 1H, Ar—H), 8.41 (s, 1H, NH), 12.98 (br s, 1H, NH). Anal. calcd. for $C_{16}H_{11}Cl_2N_5$. 1.3HCl: C, 49.04; H, 3.17; N, 17.88. Found: C, 48.90; H, 3.47; N, 17.77.

Example 18 8-Chloro-$N^4$-(p-tolyl)-1H-pyrazolo[4,3-c]quinoline-3,4-diamine 11 ($R^1$=6-Cl, $R^2$=4'-Me)

Yield: 46%. mp: 261° C. $^1$H-NMR (400 MHz, DMSO-$d_6$): 2.30 (s, 3H, Me), 5.67 (br s, 2H, $NH_2$), 7.16 (d, 2H, J=8.0 Hz, Ar—H), 7.49 (d, 1H, J=7.6 Hz, Ar—H), 7.60 (d, 1H, J=8.8 Hz, Ar—H), 7.80 (d, 2H, J=8.0 Hz, Ar—H), 8.13 (s, 1H, Ar—H), 8.23 (s, 1H, NH), 12.95 (br s, 1H, NH). Anal, calcd. for $C_{17}H_{14}ClN_5$. 1.3HCl: C, 54.45; H, 4.14; N, 18.68. Found: C, 54.24; H, 4.36; N, 18.38.

Example 19 8-Bromo-$N^4$-(4-chlorophenyl)-1H-pyrazolo[4,3-c]quinoline-3,4-diamine 12 ($R^1$=6-Br, $R^2$=4'-Cl)

Yield: 50%. mp: 264° C. (dec.). $^1$H-NMR (400 MHz, DMSO-$d_6$): 5.71 (br s, 2H, $NH_2$), 7.39 (d, 2H, J=8.8 Hz, Ar—H), 7.56-7.63 (m, 2H, Ar—H), 8.00 (d, 2H, J=8.8 Hz, Ar—H), 8.30 (s, 1H, Ar—H), 8.40 (s, 1H, NH), 12.95 (br s, 1H, NH).

Example 20 S-Bromo-$N^4$-(p-tolyl)-1H-pyrazolo[4,3-c]quinoline-3,4-diamine 13 ($R^1$=6-Br, $R^2$=4'-Me)

Yield: 73%. mp: 276° C. $^1$H-NMR (400 MHz, DMSO): 2.30 (s, 3H, Me), 5.68 (br s, 2H, $NH_2$), 7.17 (d, 2H, J=8.4 Hz, Ar—H), 7.52-7.61 (m, 2H, Ar—H), 7.79 (d, 2H, J=6.8 Hz, Ar—H), 8.26 (br s, 2H, Ar—H and NH), 12.96 (br s, 1H, NH).

Example 21 3-Amino-4-anilino-1H-pyrazolo[4,3-c]quinoline 14 ($R^1$=$R^2$=H) (3509)

Yield 86%. Mp.: 256-258° C. (lit. 258-259° C.)[28]. $^1$H-NMR (400 MHz, DMSO-$d_6$): 5.62 (br s, 2H, $NH_2$), 6.99-7.03 (m, 1H, Ar—H), 7.27-7.37 (m, 3H, Ar—H), 7.48-7.52 (m, 1H, Ar—H), 7.63 (d, 1H, J=8.0 Hz, Ar—H), 7.97 (d, 2H, J=8.0 Hz, Ar—H), 8.06 (d, 1H, J=8.0 Hz, Ar—H), 8.24 (s, 1H, NH), 12.92 (s, 1H, NH). Anal. calcd for $C_{16}H_{13}N_5$: C, 69.80, H, 4.76, N, 25.44; found: C, 70.11, H, 5.01, N, 25.32.

Example 22 3-Amino-4-(4-hydroxyphenylamino)-1H-pyrazolo[4,3-c]quinoline 15 ($R^1$=H, $R^2$=4'-OH) (3565)

Yield 82%. Mp.: 347-349° C. (December). $^1$H-NMR (400 MHz, DMSO-$d_6$): 6.96 (d, 2H, J=8.8 Hz, Ar—H), 7.36 (d, 2H, J=8.4 Hz, Ar—H), 7.39-7.43 (m, 1H, Ar—H), 7.51-7.56 (m, 1H, Ar—H), 7.79-7.81 (m, 1H, Ar—H), 8.14 (m, 1H, Ar—H), 9.96 (br s, 1H, NH), 10.59 (br s, 1H, OH), 12.21 (br s, 1H, NH). Anal, calcd for $C_{16}H_{13}N_5O.2.0H_2O$: C, 58.70, H, 5.24, N, 21.40; found: C, 58.47, H, 5.24, N, 21.70.

Example 23 3-Amino-4-(4-aminophenylamino)-1H-pyrazolo[4,3-c]quinoline 16 ($R^1$=H, $R^2$=4'-$NH_2$) (4522)

Yield 61%. Mp.: 355-356° C. $^1$H-NMR (400 MHz, DMSO-$d_6$): 5.57 (br s, 2H, $NH_2$), 6.35 (br s, 2H, NH), 6.71 (d, 2H, J=8.8 Hz, Ar—H), 7.17 (d, 2H, J=8.0 Hz, Ar—H), 7.39-7.51 (m, 3H, Ar—H), 7.77-7.81 (m, 1H, Ar—H), 8.08 (br s, 1H, NH), 10.41 (br s, 1H, NH), 10.98 (br s, 1H, NH), 12.96 (br s, 1H, NH).

Example 24 3-Amino-4-(4-fluorophenylamino)-1H-pyrazolo[4,3-c]quinoline 17 ($R^1$=H, $R^2$=4'-F) (3511)

Yield 79%. Mp.: 266-268° C. $^1$H-NMR (400 MHz, DMSO-$d_6$): 5.64 (br s, 2H, $NH_2$), 7.16-7.21 (m, 2H, Ar—H), 7.27-7.30 (m, 1H, Ar—H), 7.47-7.51 (m, 1H, Ar—H), 7.60 (d, 1H, J=8.0 Hz, Ar—H), 7.96-7.99 (m, 2H, Ar—H), 7.61 (d, 1H, J=7.6 Hz, Ar—H), 8.25 (br s, 1H, NH), 12.91 (br s, 1H, NH). Anal. calcd for $C_{16}H_{12}FN_5$: C, 65.52, H, 4.12, N, 23.88; found: C, 65.52, H, 4.39, N, 23.63.

Example 25 3-Amino-4-(4-trifluoromethylphenylamino)-1H-pyrazolo[4,3-c]quinoline 18 ($R^1$=H, $R^2$=4'-$CF_3$) (3508)

Yield 75%. Mp.: 251-252° C. $^1$H-NMR (400 MHz, DMSO-$d_6$): 5.68 (br s, 2H, $NH_2$), 7.34-7.38 (m, 1H, Ar—H), 7.53-7.57 (m, 1H, Ar—H), 7.68-7.72 (m, 3H, Ar—H), 8.40

(d, 1H, J=7.6 Hz, Ar—H), 8.20 (d, 2H, J=8.8 Hz, Ar—H), 8.61 (br s, 1H, NH), 13.00 (br s, 1H, NH). Anal, calcd for $C_{17}H_{12}F_3N_5$: C, 59.48, H, 3.52, N, 20.40; found: C, 59.55, H, 3.57, N, 20.26.

Example 26 3-Amino-4-(4-methoxyphenylamino)-1H-pyrazolo[4,3-c]quinoline 19 ($R^1$=H, $R^2$=4'-OMe) (3506)

Yield 81%. Mp.: 228-230° C. (lit. 235-237° C.)[28]. $^1$H-NMR (400 MHz, DMSO-$d_6$): 3.67 (s, 3H, OMe), 5.62 (br s, 2H, NH$_2$), 6.94 (d, 2H, J=9.2 Hz, Ar—H), 7.23-7.26 (m, 1H, Ar—H), 7.44-7.48 (m, 1H, Ar—H), 7.56 (d, 1H, J=8.0 Hz, Ar—H), 7.83 (d, 2H, J=7.6 Hz, Ar—H), 8.03 (d, 1H, J=8.4 Hz, Ar—H), 8.10 (br s, 1H, NH), 12.86 (br s, 1H, NH). Anal, calcd for $C_{17}H_{15}N_5O.0.1H_2O$: C, 66.47, H, 5.00, N, 22.80; found: C, 66.39, H, 4.98, N, 22.94.

Example 27 3-Amino-4-(4-methylthiophenylamino)-1H-pyrazolo[4,3-c]quinoline 20 ($R^1$=H, $R^2$=4'-SMe) (3512)

Yield 80%. Mp.: 269-271° C. $^1$H-NMR (400 MHz, DMSO-$d_6$): 2.48 (s, 3H, SMe), 5.63 (br s, 2H, NH$_2$), 7.29 (d, 1H, J=8.8 Hz, Ar—H), 7.48-7.51 (m, 1H, Ar—H), 7.61 (d, 1H, J=8.0 Hz, Ar—H), 7.95 (d, 1H, J=8.4 Hz, Ar—H), 8.05 (d, 1H, J=7.6 Hz, Ar—H), 8.24 (br s, 1H, NH), 12.91 (br s, 1H, NH). Anal, calcd for $C_{17}H_{15}N_5S.0.1HCl$: C, 62.82, H, 4.68, N, 21.54; found: C, 62.66, H, 4.72, N, 21.14.

Example 28 3-Amino-4-(4-nitrophenylamino)-1H-pyrazolo[4,3-c]quinoline 21 ($R^1$=H, $R^2$=4'-NO$_2$) (3515)

Yield 36%. Mp.: 303-305° C. (December). $^1$H-NMR (400 MHz, DMSO-$d_6$): 5.73 (br s, 2H, NH$_2$), 7.40-7.43 (m, 1H, Ar—H), 7.58-7.61 (m, 1H, Ar—H), 7.78 (d, 1H, J=7.6 Hz, Ar—H), 8.14 (d, 1H, J=8.0 Hz, Ar—H), 8.25 (s, 4H, Ar—H), 9.10 (br s, 1H, NH), 13.08 (br s, 1H, NH). Anal, calcd for $C_{16}H_{12}N_6O_2.0.3HCl$: C, 58.01, H, 3.73, N, 25.37; found: C, 57.72, H, 4.03, N, 24.98.

Example 29 4-(3-Amino-1H-pyrazolo[4,3-c]quinolin-4-ylamino)benzoic acid 22 ($R^1$=H, $R^2$=4'-COOH) (3564)

Yield 76%. Mp.: 362-364° C. $^1$H-NMR (400 MHz, DMSO-$d_6$): 5.65 (br s, 2H, NH$_2$), 7.47-7.51 (m, 1H, Ar—H), 7.59-7.63 (m, 1H, Ar—H), 7.74-7.78 (m, 3H, Ar—H), 8.07 (d, 2H, J=8.4 Hz, Ar—H), 8.19 (d, 1H, J=8.0 Hz, Ar—H), 11.21 (br s, 1H, NH), 12.17 (br s, 1H, NH), 12.95 (br s, 1H, COOH). Anal, calcd for $C_{17}H_{13}N_5O_2.HCl$: C, 57.39, H, 3.97, N, 19.68; found: C, 57.45, H, 3.84, N, 19.76.

Example 30 3-Amino-4-(4-acetylphenylamino)-1H-pyrazolo[4,3-c]quinoline 23 ($R^1$=H, $R^2$=4'-COMe) (3505)

Yield 83%. Mp.: 249-251° C. $^1$H-NMR (400 MHZ, DMSO-$d_6$): 2.55 (s, 3H, Me), 5.67 (br s, 2H, NH$_2$), 7.35-7.38 (m, 1H, Ar—H), 7.54-7.58 (m, 1H, Ar—H), 7.72 (d, 1H, J=8.0 Hz, Ar—H), 7.97 (d, 2H, J=8.8 Hz, Ar—H), 8.10-8.15 (m, 3H, Ar—H), 8.65 (br s, 1H, NH), 13.01 (br s, 1H, NH). Anal, calcd for $C_{18}H_{15}N_5O.0.1HCl$: C, 67.35, H, 4.74, N, 21.82; found: C, 67.22, H, 4.82, N, 21.57.

Example 31 3-Amino-4-(3-hydroxyphenylamino)-1H-pyrazolo[4,3-c]quinoline 24 ($R^1$=H, $R^2$=3'-OH) (4518)

Yield 84%. Mp.: 319-321° C. $^1$H-NMR (400 MHz, DMSO-$d_6$): 6.82 (d, 1H, J=7.6 Hz, Ar—H), 6.98 (d, 2H, J=6.8 Hz, Ar—H), 7.30-7.34 (m, 1H, Ar—H), 7.42-7.46 (m, 1H, Ar—H), 7.54-7.58 (m, 1H, Ar—H), 7.78 (d, 1H, J=7.6 Hz, Ar—H), 8.15 (s, 1H, Ar—H), 9.95 (s, 1H, NH), 10.81 (br s, 1H, OH), 11.78 (br s, 1H, NH). Anal, calcd for $C_{16}H_{13}N_5O.1.25HCl$: C, 57.03, H, 4.27, N, 20.79; found: C, 56.95, H, 4.62, N, 21.02.

Example 32 ($N^4$-(m-Tolyl)-1H-pyrazolo[4,3-c]quinoline-3,4-diamine 25 ($R^1$=H, $R^2$=3'-Me)

Yield: 50%. mp: 281-282° C. $^1$H-NMR (400 MHZ, DMSO-$d_6$): 2.39 (s, 3H, Me), 7.23 (d, 1H, J=7.6 Hz, Ar—H), 7.38-7.47 (m, 4H, Ar—H), 7.57 (dd, 1H, J=8.0 Hz, Ar—H), 7.78 (d, 1H, J=8.0 Hz, Ar—H), 8.16 (d, 1H, J=6.4 Hz, Ar—H), 10.88 (br s, 1H, NH), 11.70 (br s, 1H, NH). Anal, calcd. for $C_{17}H_{15}N_5.1.1HCl$: C, 61.95; H, 4.93; N, 21.25. Found: C, 61.95; H, 4.67; N, 21.18.

Example 33 $N^4$-(3-Chlorophenyl)-1H-pyrazolo[4,3-c]quinoline-3,4-diamine 26 ($R^1$=H, $R^2$=3'-Cl)

Yield: 57%. mp: 227-229° C. $^1$H-NMR (400 MHz, DMSO-$d_6$): 5.66 (br s, 2H, NH$_2$), 7.05 (dd, 1H, J=8.0, 1.6 Hz, Ar—H), 7.34-7.39 (m, 2H, Ar—H), 7.54 (m, 1H, Ar—H), 7.67 (d, 1H, J=7.6 Hz, Ar—H), 7.89 (d, 1H, J=12 Hz, Ar—H), 8.09 (d, 1H, J=7.6 Hz, Ar—H), 8.27 (s, 1H, Ar—H), 8.39 (br s, 1H, NH), 12.97 (br s, 1H, NH). Anal, calcd. for $C_{16}H_{12}ClN_5$: C, 62.04; H, 3.90; N, 22.61. Found: C, 61.91; H, 3.88; N, 22.40.

Example 34 3-Amino-4-(3-methoxyphenylamino)-1H-pyrazolo[4,3-c]quinoline, 27 ($R^1$=H, $R^2$=3'-OMe) (3514)

Yield 76%. Mp.: 184-186° C. $^1$H-NMR (400 MHz, DMSO-$d_6$): 3.81 (s, 3H, OMe), 5.63 (br s, 2H, NH$_2$), 6.58-6.61 (m, 1H, Ar—H), 7.22-7.26 (m, 1H, Ar—H), 7.29-7.33 (m, 1H, Ar—H), 7.44 (d, 1H, J=8.0 Hz, Ar—H), 7.50-7.54 (m, 1H, Ar—H), 7.65 (d, 1H, J=8.0 Hz, Ar—H), 7.90 (s, 1H, Ar—H), 8.07 (d, 1H, J=7.6 Hz, Ar—H), 8.24 (s, 1H, NH), 12.95 (br s, 1H, NH). Anal, calcd for $C_{17}H_{15}N_5O$: C, 66.87, H, 4.95, N, 22.94; found: C, 66.64, H, 4.98, N, 22.68.

Example 35 3-Amino-4-(3-acetylphenylamino)-1H-pyrazolo[4,3-c]quinoline, 28 ($R^1$=H, $R^2$=3'-COMe) (3117)

Yield 84%. Mp.: >380° C. $^1$H-NMR (400 MHz, DMSO-$d_6$): 2.63 (s, 3H, Me), 7.45-7.49 (m, 1H, Ar—H), 7.57-7.60 (m, 1H, Ar—H), 7.68-7.72 (m, 1H, Ar—H), 7.76 (d, 1H, J=8.4 Hz, Ar—H), 7.89 (d, 1H, J=8.8 Hz, Ar—H), 7.97 (d, 1H, J=7.6 Hz, Ar—H), 8.17-8.20 (m, 2H, Ar—H), 11.05 (br s, 1H, NH), 11.85 (br s, 1H, NH). Anal, calcd for $C_{18}H_{15}N_5O.0.5H_2O$: C, 66.23, H, 4.95, N, 21.46; found: C, 66.31, H, 4.66, N, 21.26.

Example 36 3-Amino-4-(2-hydroxyphenylamino)-1H-pyrazolo[4,3-c]quinoline, 29 ($R^1$=H, $R^2$=2'-OH) (3507)

Yield 64%. Mp.: 156-157° C. $^1$H-NMR (400 MHz, DMSO-$d_6$): 5.51 (br s, 2H, NH$_2$), 6.84-6.99 (m, 3H, Ar—H), 7.29-7.32 (m, 1H, Ar—H), 7.50-7.53 (m, 1H, Ar—H), 7.60 (d, 1H, J=7.2 Hz, Ar—H), 8.06 (d, 2H, J=7.6 Hz, Ar—H), 8.43 (s, 1H, NH), 11.22 (br s, 1H, OH), 13.06 (s, 1H, NH). Anal, calcd for $C_{16}H_{13}N_5O \cdot 0.5H_2O$: C, 63.98, H, 4.71, N, 23.32; found: C, 63.66, H, 4.65, N, 23.33.

Example 37 $N^4$-(o-Tolyl)-1H-pyrazolo[4,3-c]quinoline-3,4-diamine 30 ($R^1$=H, $R^2$=2'-Me)

Yield: 31%. mp: 228-230° C. $^1$H-NMR (400 MHz, DMSO-$d_6$): 2.31 (s, 3H, Me), 5.48 (br s, 2H, NH$_2$), 7.02-7.05 (m, 1H, Ar—H), 7.23-7.27 (m, 3H, Ar—H), 7.45 (br s, 1H, Ar—H), 7.55 (d, 1H, J=7.6 Hz, Ar—H), 8.05 (br s, 2H, Ar—H), 8.31 (br s, 1H, NH), 12.96 (br s, 1H, NH). Anal, calcd. for $C_{17}H_{15}N_5 \cdot 0.2 H_2O$: C, 69.68; H, 5.30; N, 23.90. Found: C, 69.95; H, 5.17; N, 23.70.

Example 38 $N^4$-(2-Chlorophenyl)-1H-pyrazolo[4,3-c]quinoline-3,4-diamine 31 ($R^1$=H, $R^2$=2'-Cl)

Yield: 52%. mp: 243-244° C. $^1$H-NMR (400 MHZ, DMSO-$d_6$): 5.46 (br s, 2H, NH$_2$), 7.43-7.47 (m, 1H, Ar—H), 7.52-7.59 (m, 3H, Ar—H), 7.71-7.75 (m, 2H, Ar—H), 7.79 (d, 1H, J=8.0 Hz, Ar—H), 8.17 (d, 1H, J=7.6 Hz, Ar—H), 8.30 (br s, 1H, NH), 11.45 (br s, 1H, NH).

Example 39 3-Amino-4-(2-methoxyphenylamino)-1H-pyrazolo[4,3-c]quinoline, 32 ($R^1$=H, $R^2$=2'-OMe) (3510)

Yield 69%. Mp.: 210-211° C. $^1$H-NMR (400 MHz, DMSO-$d_6$) 5.22 (s, 2H, NH$_2$), 6.96-7.08 (m, 3H, Ar—H), 7.29-7.32 (m, 1H, Ar—H), 7.50-7.54 (m, 1H, Ar—H), 7.69 (d, 1H, J=8.0 Hz, Ar—H), 8.06 (d, 1H, J=8.0 Hz, Ar—H), 8.57 (s, 1H, NH), 8.99 (d, 1H, J=7.2 Hz, Ar—H), 13.03 (s, 1H, NH). Anal, calcd for $C_{17}H_{15}N_5O \cdot 0.45H_2O$: C, 65.13, H, 5.12, N, 22.35; found: C, 65.31, H, 5.03, N, 21.99.

Example 40 3-Amino-1H-pyrazolo[4,3-c]quinolin-4(5H)-one 33

A mixture of 3a (0.22 g, 1.0 mmol) and 36% HCl (1 mL) in DMF (30 mL) was refluxed for 2 h (TLC monitoring). The mixture was evaporated in vacuo, treated with H$_2$O (20 mL), filtered, and the crude solid was recrystallized from EtOH to give 33 (0.15 g, 75%) as a yellow solid. Mp.: 316-318° C. $^1$H-NMR (400 MHz, DMSO-$d_6$): 5.73 (br s, 2H, NH$_2$), 7.60-7.72 (m, 2H, Ar—H), 7.89 (d, 1H, J=8.0 Hz, Ar—H), 8.24 (dd, 1H, J=8.0, 1.6 Hz, Ar—H), 13.23 (br s, 1H, NH).

Example 41 1-(4-oxo-4,5-dihydro-1H-pyrazolo[4,3-c]quinolin-3-yl)-3-phenylurea 34

A mixture of 45 (0.20 g, 1.0 mmol) and phenyl isocyanate (0.36 g, 3.0 mmol) in acetonitrile (8 mL) was stirred at room temperature for 2 hrs (TLC monitoring). The precipitate was collected by filtration, washed with acetonitrile and dried to yield white solid. The crude product was recrystallized with EtOH to give 34 (0.23 g, 72%). Mp.: 240-242° C. $^1$H-NMR (400 MHz, TFA-d): 7.39-7.44 (m, 1H, Ar—H), 7.49-7.52 (m, 4H, Ar—H), 7.56-7.63 (m, 2H, Ar—H), 7.84-7.88 (m, 1H, Ar—H), 8.20 (d, 1H, J=8.0 Hz, Ar—H).

Example 42 1-(4-Methoxyphenyl)-3-(4-oxo-4,5-dihydro-1H-pyrazolo[4,3-c]-quinolin-3-yl)urea 35

Compound 35 was obtained from 33 and 4-methoxyphenyl isocyanate as described for 34 in 47% yield. Mp.: 224-225° C. $^1$H-NMR (400 MHz, TFA-d): 3.90 (s, 3H, OCH$_3$), 7.02 (d, 2H, J=8.8 Hz, Ar—H), 7.37 (d, 2H, J=8.8 Hz, Ar—H), 7.43-7.46 (m, 2H, Ar—H), 7.68-7.72 (m, 1H, Ar—H), 8.02 (d, 1H, J=8.0 Hz, Ar—H).

Example 43 1-{4-[(4-Chlorophenyl)amino]-1H-pyrazolo[4,3-c]quinolin-3-yl}-3-phenylurea 36

Compound 36 was obtained from 4 and phenyl isocyanate as described for 34 in 70% yield. Mp.: 282-283° C. $^1$H-NMR (400 MHz, TFA-d): 7.98 (d, 2H, J=6.8, Ar—H), 8.06-8.29 (m, 10H, Ar—H), 8.92 (d, 1H, J=7.6 Hz, Ar—H).

Example 44 1-Phenyl-3-[4-(p-tolylamino)-1H-pyrazolo[4,3-c]quinolin-3-yl]urea 37

Compound 37 was obtained from 5 and phenyl isocyanate as described for 34 in 73% yield. Mp.: 212-213° C. $^1$H-NMR (400 MHz, TFA-d): 2.51 (s, 3H, CH$_3$), 7.38-7.58 (m, 11H, Ar—H), 7.66-7.70 (m, 1H, Ar—H), 8.33 (d, 1H, J=7.6 Hz, Ar—H).

Example 45 1-{4-[(4-Chlorophenyl)amino]-1H-pyrazolo[4,3-c]quinolin-3-yl}-3-(4-methoxyphenyl)urea 38

Compound 38 was obtained from 4 and 4-methoxyphenyl isocyanate as described for 34 in 80% yield. Mp.: 211-212° C. $^1$H-NMR (400 MHz, TFA-d): 4.13 (s, 3H, OCH$_3$), 7.26 (d, 2H, J=8.4 Hz, Ar—H), 7.45 (d, 1H, J=8.4 Hz, Ar—H), 7.54-7.77 (m, 8H, Ar—H), 8.39 (d, 1H, J=8.0 Hz, Ar—H).

Example 46 1-(4-Methoxyphenyl)-3-[4-(p-tolylamino)-1H-pyrazolo[4,3-c]-quinolin-3-yl]urea 39

Compound 39 was obtained from 5 and 4-methoxyphenyl isocyanate as described for 34 in 85% yield. Mp.: 163-164° C. $^1$H-NMR (400 MHz, TFA-d): 2.89 (s, 3H, CH$_3$), 4.43 (s, 3H, OCH$_3$), 7.56 (d, 2H, J=9.2 Hz, Ar—H), 7.73-7.78 (m, 3H, Ar—H), 7.86-7.95 (m, 5H, Ar—H), 8.03-8.06 (m, 1H, Ar—H), 8.68 (d, 1H, J=8.0 Hz, Ar—H).

Example 47 Specific Inhibit E. coli β-Glucuronidase Activity by Pyrazolo[4,3-c]Quinoline Derivatives To identify more potent and specific eβG inhibitors, we have screened a large number of compounds through the high throughput screening (HTS) and discovered certain pyrazolo[4,3-c]quinoline derivatives (TCH-series, Formula I) which can specifically inhibit the activity of eβG but not effect hβG (see Table 1).

Figure 1B:
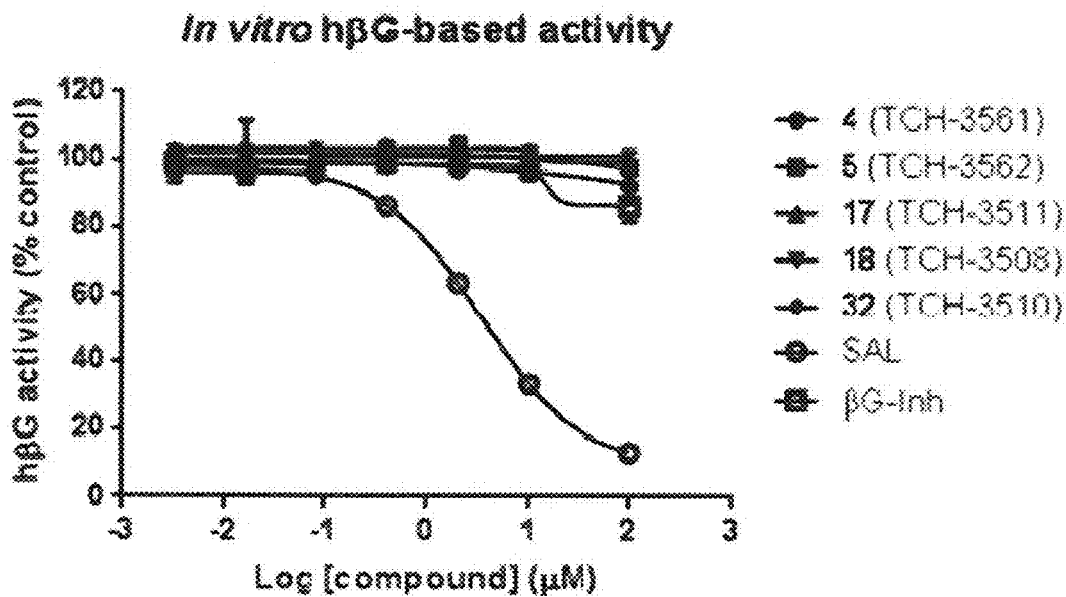

The pyrazolo[4,3-c]quinoline derivatives were examined for their inhibition against eβG or hβG activity. Purified recombinant eβG or hβG proteins were incubated with serial dilution of the inhibitors, respectively. The βG activity was determined by color development of a βG substrate, pNPG. The hydrolysis product of pNPG, PNP was measured by $OD_{420}$. Results are displayed as percent inhibition of βG activity compared with control without inhibitors treated (see Table 1 below). Our data shows that inhibitors, including 4 (TCH-3561), 5 (TCH-3562), 17 (TCH-3511), and 32 (TCH-3510) selectively inhibited eβG activity but not hβG. These compounds displayed better inhibition efficacy of eβG activity than βG-Inh (FIG. 1).

TABLE 1

Inhibitory activities of Pyrazolo[4,3-c]quinolines against eβG and hβG

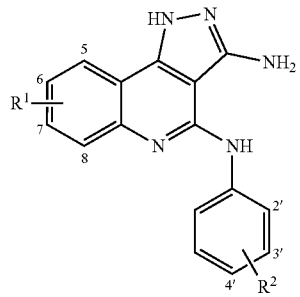

Formula I

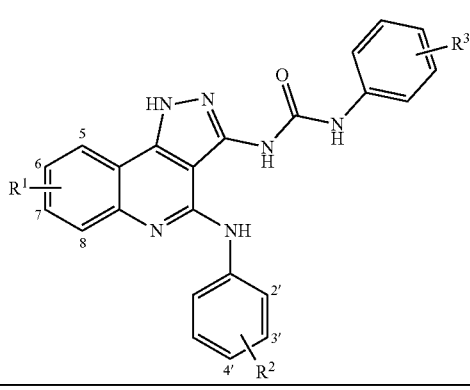

Formula II

| Coumped | R¹ | R² | R³ | Percent activity of E. coli-glucuronidase at 10 μM (%) | Percent activity of human liver-glucuronidase at 10 μM (%) |
|---|---|---|---|---|---|
| 4 (TCH-3561) | H | 4'-Cl | | 4.5 ± 0.71 | 113 ± 2.83 |
| 5 (TCH-3562) | H | 4'-Me | | 4.5 ± 0.71 | 110.5 ± 2.12 |
| 6 (TCH-2471) | 8-Me | 4'-Cl | | 6 ± 1 | 78.5 ± 0.71 |
| 7 (TCH-2472) | 8-Me | 4'-Me | | 3 ± 1 | 74 ± 1 |
| 8 (TCH-2469) | 7-F | 4'-Cl | | 4 ± 1 | 83.5 ± 0.71 |
| 9 (TCH-2470) | 7-F | 4'-Me | | 4 ± 1 | 81.5 ± 0.71 |
| 10 (TCH-2473) | 6-Cl | 4'-Cl | | 3 ± 1 | 77 ± 1.41 |
| 11 (TCH-2474) | 6-Cl | 4'-Me | | 3 ± 1 | 80.5 ± 2.12 |
| 12 (TCH-2475) | 6-Br | 4'-Cl | | 5 ± 1 | 79.3 ± 2.63 |
| 13 (TCH-2476) | 6-Br | 4'-Me | | 4 ± 1 | 80.21 ± 2.14 |
| 14 (TCH-3509) | H | H | | 4 ± 1 | 105.5 ± 0.71 |
| 15 (TCH-3565) | H | 4'-OH | | 7 ± 1 | 95 ± 4.24 |
| 16 (TCH-4522) | H | 4'-NH₂ | | 8 ± 1 | 82.5 ± 3.54 |
| 17 (TCH-3511) | H | 4'-F | | 5 ± 1 | 99 ± 1.41 |
| 18 (TCH-3508) | H | 4'-CF₃ | | 4.5 ± 0.71 | 106 ± 2.83 |
| 19 (TCH-3506) | H | 4'-OMe | | 3 ± 1 | 102.5 ± 2.12 |
| 20 (TCH-3512) | H | 4'-SMe | | 5 ± 1.41 | 108.5 ± 3.54 |
| 21 (TCH-3515) | H | 4'-NO₂ | | 46.5 ± 4.95 | 90.86 ± 0.32 |
| 22 (TCH-3564) | H | 4'-COOH | | 15.5 ± 1.71 | 95 ± 4.24 |
| 23 (TCH-3505) | H | 4'-COMe | | 3 ± 1 | 104 ± 1.41 |
| 24 (TCH-4518) | H | 3'-OH | | 13.5 ± 0.71 | 105 ± 1.41 |
| 25 (LWF-2503) | H | 3'-Me | | 69.9 ± 0.02 | 102 ± 2.08 |
| 26 (TCH-2479) | H | 3'-Cl | | 14.9 ± 2.31 | 97.78 ± 0.01 |
| 27 (TCH-3514) | H | 3'-OMe | | 8 ± 1.41 | 107 ± 1.41 |
| 28 (TCH-3117) | H | 3'-COMe | | 91 ± 1 | 93 ± 2.83 |
| 29 (TCH-3507) | H | 2'-OH | | 7 ± 1 | 104.5 ± 2.12 |
| 30 (TCH-2477) | H | 2'-Me | | 17.04 ± 2.1 | 95.69 ± 0.01 |
| 31 (TCH-2482) | H | 2'-Cl | | 29.67 ± 3 | 79.81 ± 0.01 |
| 32 (TCH-3510) | H | 2'-OMe | | 3.5 ± 0.71 | 103 ± 1.41 |
| 34 | H | | H | 86 ± 1 | 82 ± 1.41 |
| 35 | H | | OMe | 52 ± 4.24 | 81.5 ± 0.71 |
| 36 | H | 4'-Cl | H | 4 ± 1 | 83.1 ± 1.29 |
| 37 | H | 4'-Me | H | 3 ± 1 | 82 ± 1.41 |
| 38 | H | 4'-Cl | OMe | 4 ± 1 | 85.5 ± 0.71 |
| 39 | H | 4'-Me | OMe | 3.5 ± 0.71 | 87.5 ± 2.12 |
| βG-Inh[b] | | | | 3 ± 1 | 93.5 ± 6.36 |

[a]Values are means ± S.D. of at least three separate experiments.
[b]βG-Inh was used as a positive control.

Example 48 In Vivo Endogenous β-Glucuronidase Activity Assay

Figure 2:
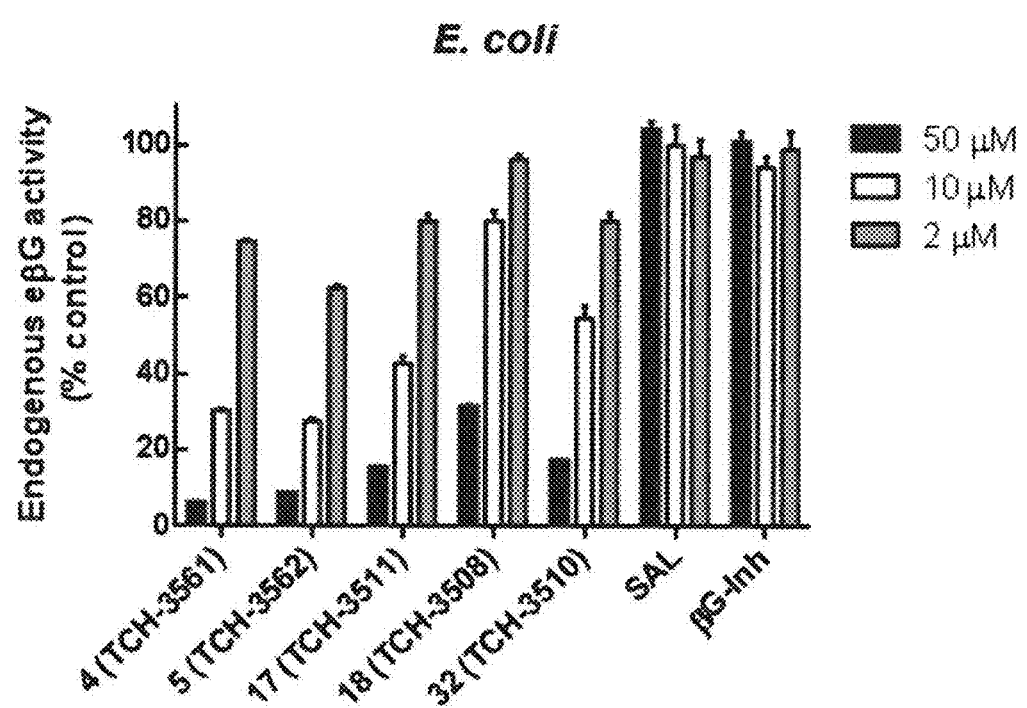
FIG. 2 shows inhibition efficacy of endogenous eβG activity by pyrazolo[4,3-c]quinoline derivatives at both low (10 μM) or high concentration (50 μM).

The pyrazolo[4,3-c]quinoline derivatives were examined for their inhibition against endogenous eβG activity. This assay is similar with the in vitro assay. BL21 *E. coli* cells were grown to an $OD_{600}$ of 0.35 in LB medium. *E. coli* were 4 times diluted and incubated with each inhibitor. The endogenous eβG activity was measured by detecting PNP as described. Results show that inhibitors including 4 (TCH-3561), 5 (TCH-3562, 17 (TCH-3511), and 32 (TCH-3510) have better inhibition efficacy of endogenous eβG activity than βG-Inh at both low (10 μM) or high concentration (50 μM) (FIG. 2).

Example 49 In Vivo Endogenous β-Glucuronidase Activity Assay

Figure 3A:
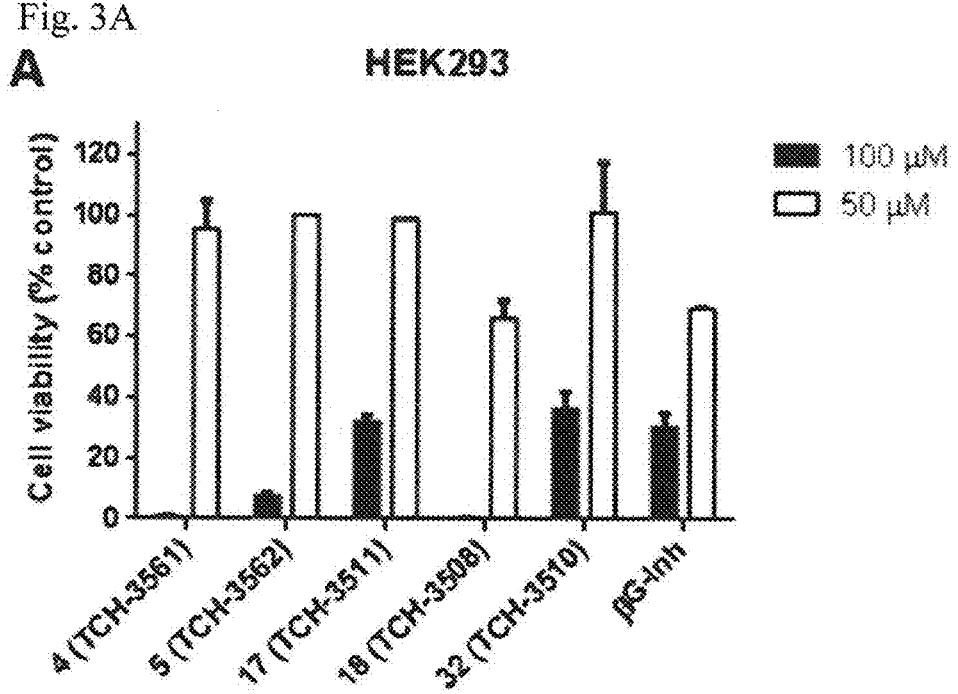
FIGS. 3A and B show cell viability assays of pyrazolo [4,3-c]quinoline derivatives against HEK293 (FIG. 3A) and CNL (FIG. 3B).
Figure 3B:
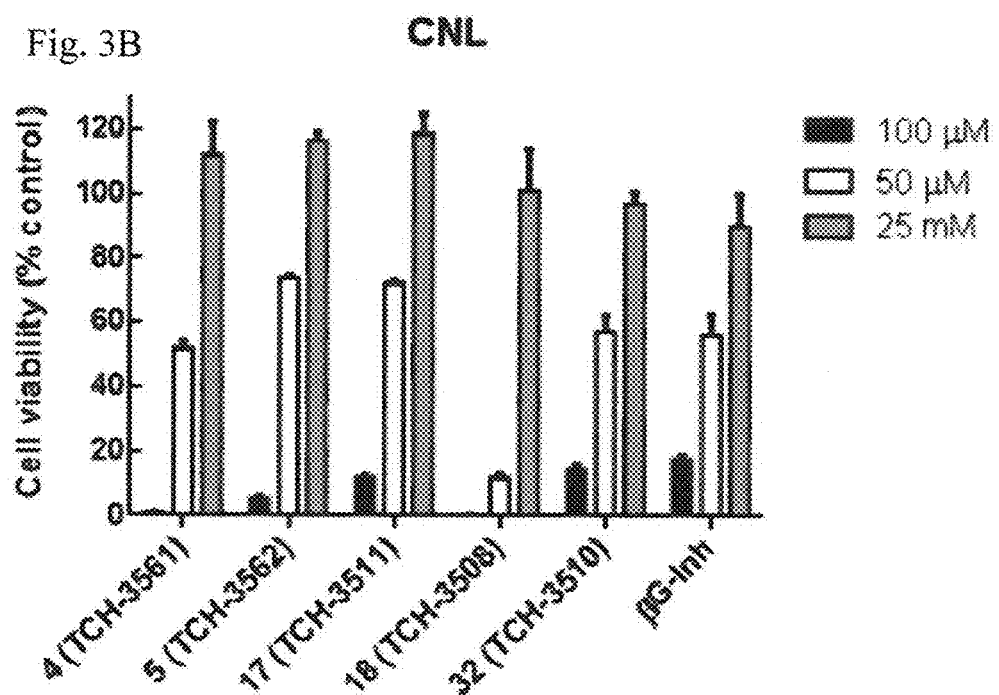

The pyrazolo[4,3-c]quinoline derivatives were examined for cytotoxicity in human cells. HEK293 human embryonic kidney cells and CNL normal liver cells were treated with inhibitors. ATPlite™ was used to quantitative evaluate the proliferative effects of the inhibitors by detecting adenosine triphosphate of the culture cells. Our results show that at low concentration of inhibitors, and that at low concentration of inhibitors, 17 (TCH-3511) or 32 (TCH-3510) treated cells similar survivability compared to the βG-Inh treated group (FIG. 3).

Example 50 *E. coli* Growth Assay

Figure 4:
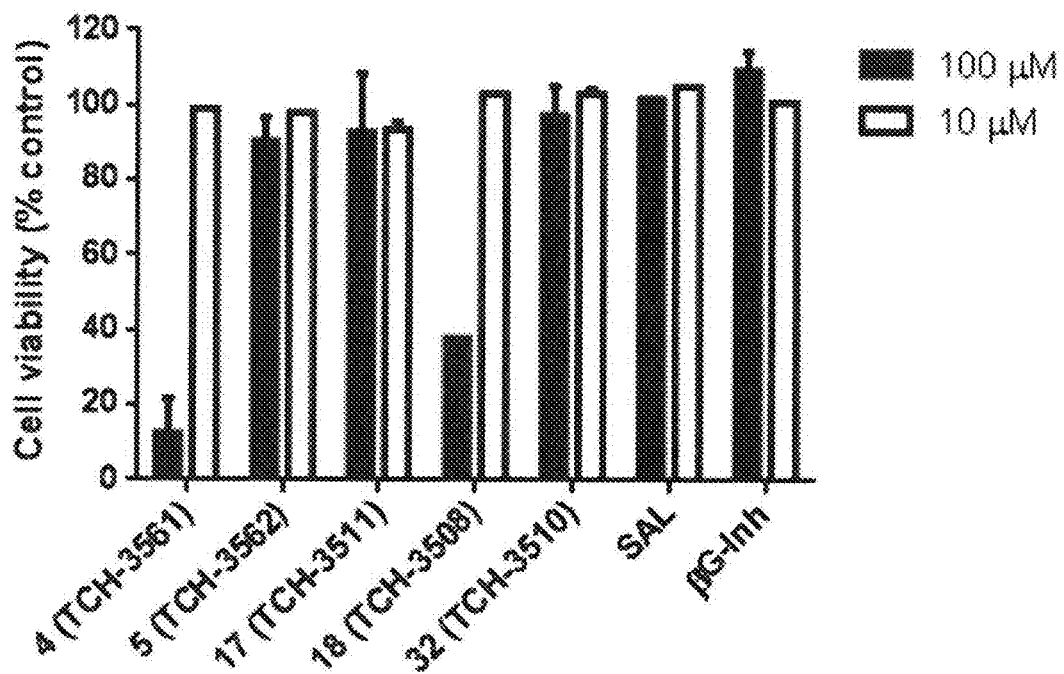
FIG. 4 shows the effects of pyrazolo[4,3-c]quinoline derivatives on *E. coli* growth.

The pyrazolo[4,3-c]quinoline derivatives were examined for effects on the growth of *E. coli*. TOP10 *E. coli* cells were grown to an $OD_{600}$ of 0.35 in LB medium and treated with each inhibitor. *E. coli* cell cultures were monitored by reading $OD_{600}$ at 6 hour after treatment. The cell viability were compared to non-inhibitor control group and shown in % control. The 5 (TCH-3562), 17 (TCH-3511) and 32 (TCH-3510) showed no effects on *E. coli* growth at high concentration (100 μM) (FIG. 4).

Figure 5A:
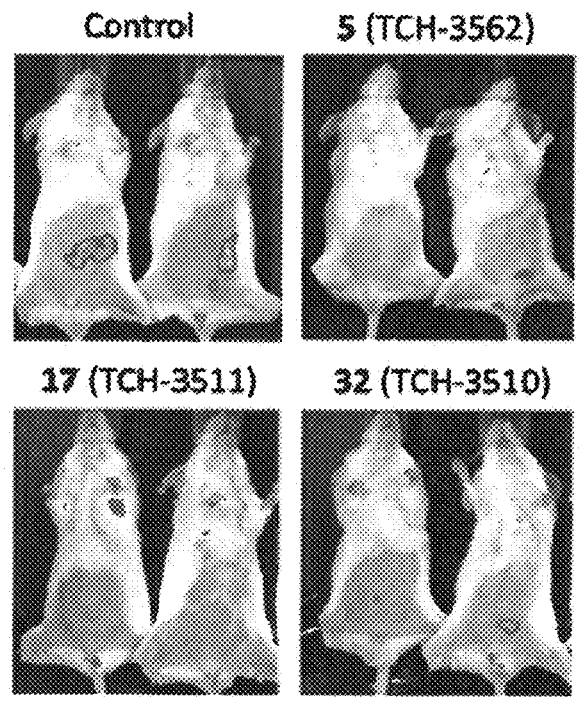
FIGS. 5A and B show the in vivo optical imaging system revealed compound 17 (TCH-3511) and 32 (THC-3510) can significantly inhibit intestinal βG activity (FIG. 5A). The inhibition of 17 (TCH-3511) is better than 32 (THC-3510) (FIG. 5B).
Figure 5B:
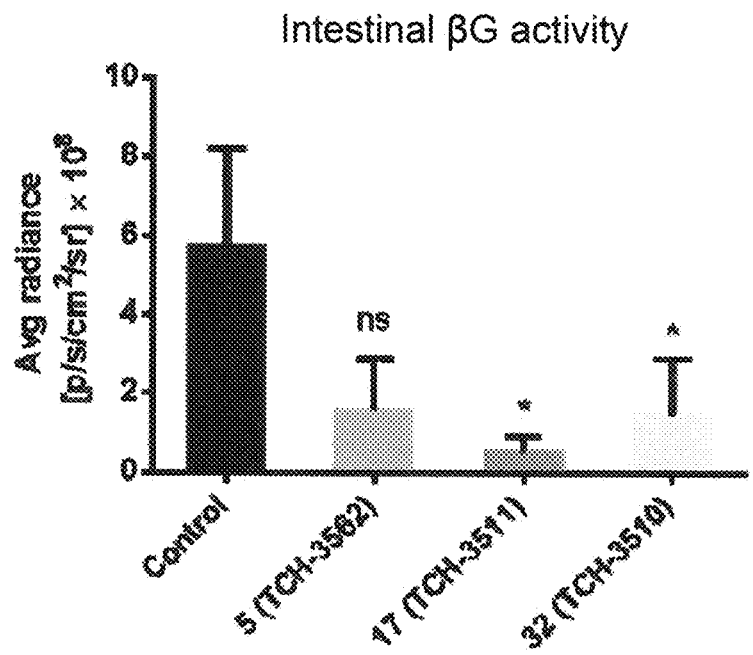

Example 51 In Vivo Image of Intestinal β-Glucuronidase Activity 17 (TCH-3511) or 32 (TCH-3510) was examined for its inhibition against intestinal βG activity in mice by in vivo image of eβG activity. 5 (TCH-3562), 17 (TCH-3511) or 32 (TCH-3510) was dissolved in $ddH_2O$. Healthy 6-10 week old female Balb/cJ mice were oral administrated with 5 (TCH-3562), 17 (TCH-3511), 32 (TCH-3510) or $ddH_2O$ per day (60 μg/200 μl) for five consecutive days. FDGlcU, a βG fluorescent pro-probe was oral feed at the sixth day. The βG activity was detected by in vivo optical imaging system. Results show that oral administration of 17 (TCH-3511) significantly reduced the fluorescence signal in the intestine, which pointed that 17 (TCH-3511) can effectively inhibit intestinal βG activity (FIG. 5).

Figure 6A:
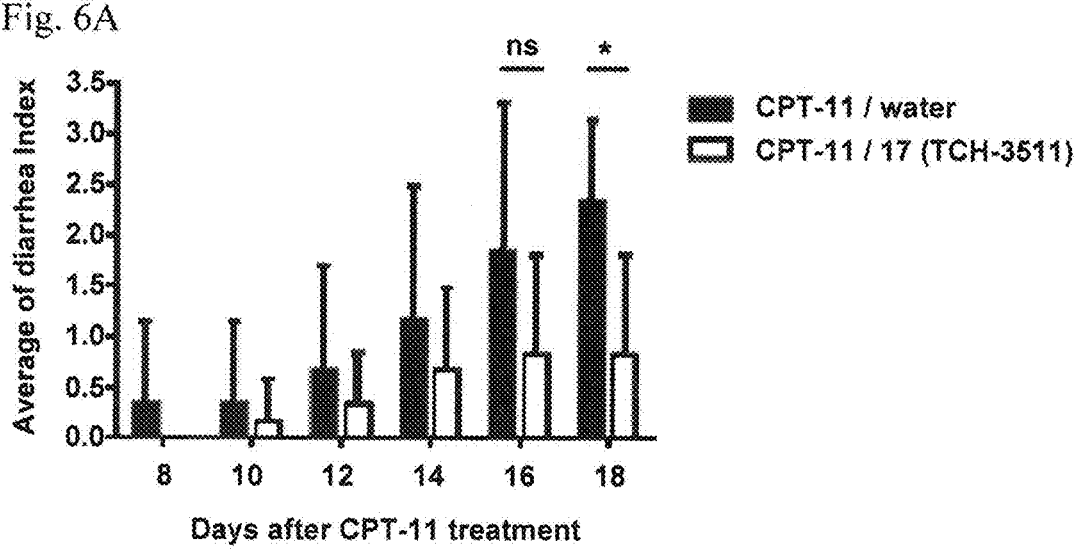
FIGS. 6A and B show the effects of 17 (TCH-3511) on diarrhea and antitumor activity of CPT-11. Mice were inoculated with CT26 cells on day −7. Either water or 17 (TCH-3511) 3 mg/kg/day was orally administrated per day throughout the experimental period (day 0 onward). Mice were given daily intraperitoneal either CPT-11 treatment (50 mg/kg/day) or saline staring on day 2. Diarrhea level and tumor size was scored every other day. (A) 17 (TCH-3511) can reduce CPT-11 induced diarrhea. (B) 17 (TCH-3511) had no effects on the anti-tumor efficacy of CPT-11 treatment.
Figure 6B:
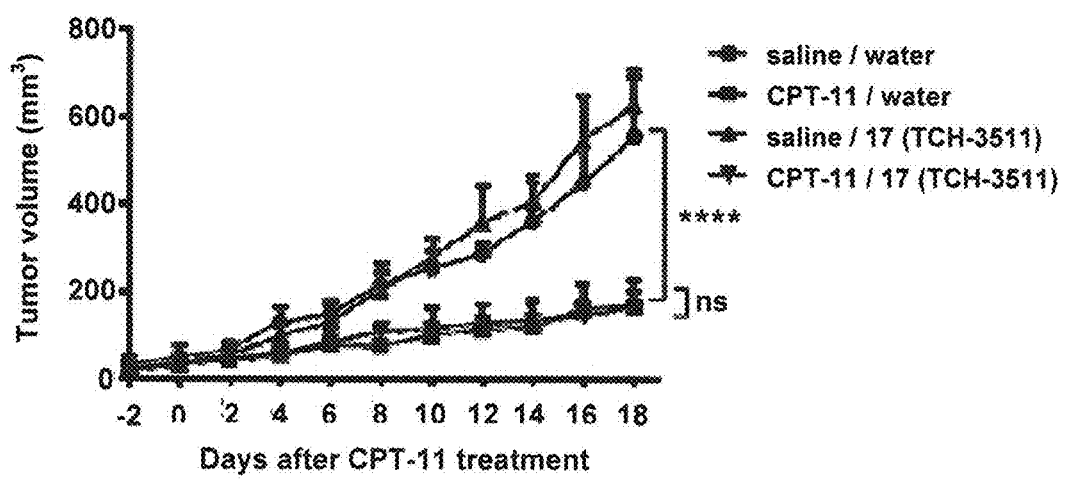

Example 52 Effects of 17 (TCH-3511) on CPT-11 Induced Diarrhea and Anti-Tumor Efficacy 17 (TCH-3511) was given to mice to test whether inhibition of intestinal βG by bacterial inhibitor 17 (TCH-3511) eliminates CPT-11-induced diarrhea and maintain the therapeutic efficacy in combination with CPT-11 in tumor-bearing mice. CT26 murine colon adenocarcinoma cells were s.c. implanted into Balb/cJ mice. After solid tumor formed, 17 (TCH-3511) (3 mg/kg/day) was provided orally along with intraperitoneal injection of CPT-11 (50 mg/kg/day). Signs of diarrhea were according to stool forms and the perianal staining of the anus. As shown in FIG. 6A, 17 (TCH-3511) can reduce CPT-11 induced diarrhea and had no effects on the anti-tumor efficacy of CPT-11 treatment (FIG. 6B).

Figure 7:
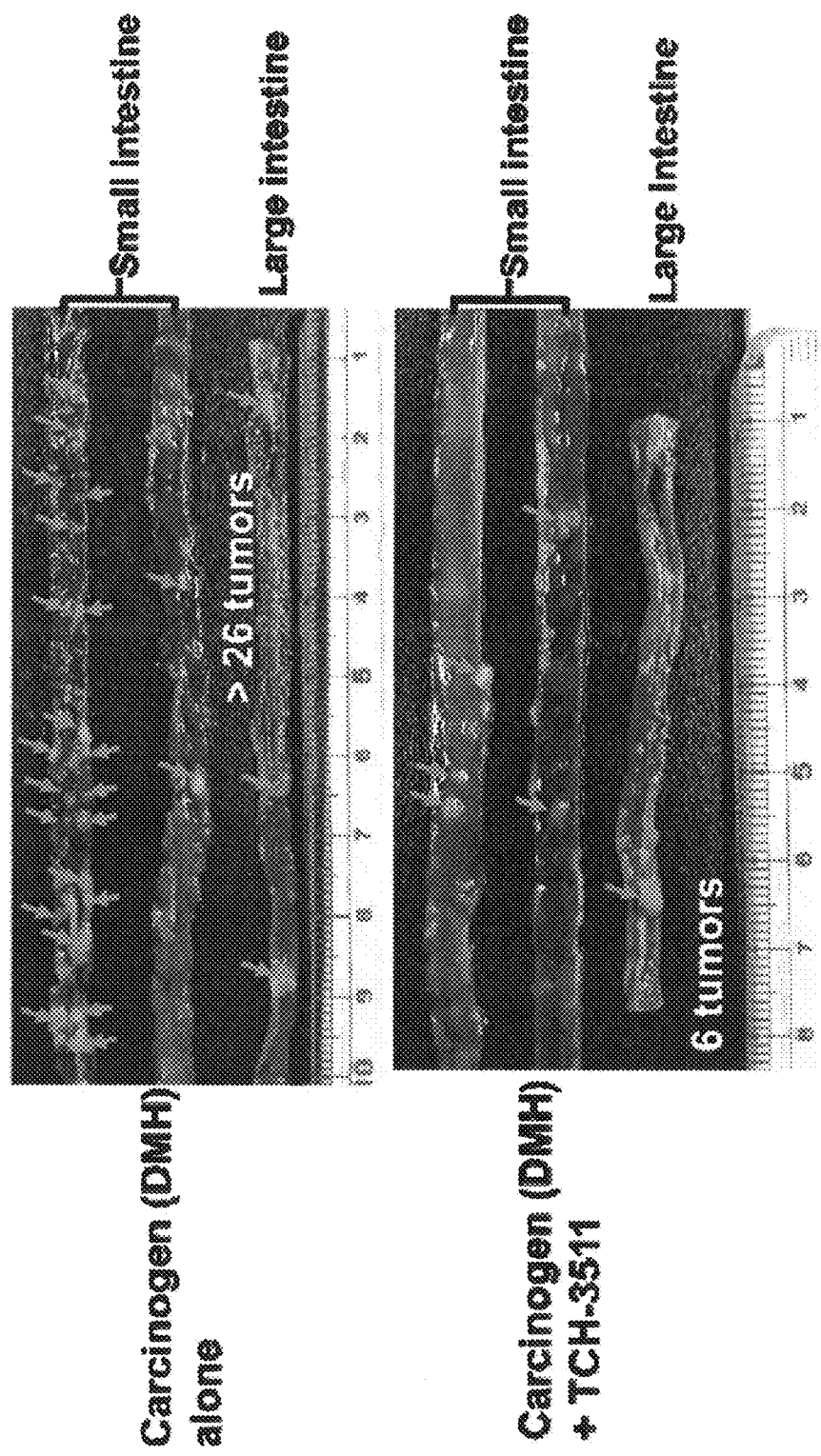
FIG. 7 shows the effects of 17 (TCH-3511) on DMH induced tumorigenesis in the intestine. Either water or 17 (TCH-3511) 3 mg/kg/day was orally administrated three times per week throughout the experimental period (8 week). Mice were given intraperitoneal DMH (30 mg/kg/week). Oral administration of 17 (TCH-3511) can reduce DMH-induced tumorigenesis.

Example 53 Effects of 17 (TCH-3511) on DMH Induced Tumorigenesis in the Intestine 17 (TCH-3511) was given to C57BL/6J-$APC^{MIN}$/J mice to check whether prevent DMH-induced intestinal damage and tumorigenesis. 17 (TCH-3511) (3 mg/kg, 3 times/week) was provided orally along with intraperitoneal injection of DMH (30 mg/kg, once/week). After 8 weeks of treatment, mice were sacrificed and the tumor in the intestine was examined. As shown in FIG. 7, more than 26 tumors were found in the DMH treated only group, whereas only six tumors in the group with 17 (TCH-3511). Therefore, 17 (TCH-3511) can reduce DMH-induced intestinal damage and prevent tumorigenesis.

What is claimed is:

1. A method for treating chemotherapy-induced diarrhea and for treating and/or reducing tumorigenesis of carcinogens induced colon carcinoma in a subject, comprising administering an effective amount of a compound of the following Formula I,

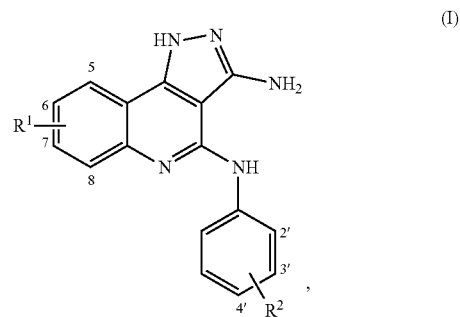

a pharmaceutical acceptable salt of the compound of the Formula I, or a solvate of the compound of the Formula I to a subject,
wherein $R^1$ is H, and $R^2$ is one of 4'-F and 4'-Me.

2. The method as claimed in claim 1, wherein the subject is receiving at least one treatment, and the at least one treatment is selected from the group consisting of angiogenic inhibitors, chemotherapy, radiation, surgery and a combination thereof.

3. The method as claimed in claim 1, wherein the compound, the pharmaceutical acceptable salt of the compound, or the solvate of the compound is administered in combination with an additional therapeutic agent including one selected from the group consisting of an anti-cancer agent metabolized through glucuronidation, an immunopotentiator and an immunomodulator.

4. The method as claimed in claim 3, wherein the compound, the pharmaceutical acceptable salt of the compound, or the solvate of the compound is administered in combination with the additional therapeutic agent in one of two states being simultaneously and separately.

* * * * *